(12) United States Patent
Chen et al.

(10) Patent No.: US 7,807,705 B2
(45) Date of Patent: Oct. 5, 2010

(54) POTENT INDOLE-3-CARBINOL-DERIVED ANTITUMOR AGENTS

(75) Inventors: Ching-Shih Chen, Upper Arlington, OH (US); Dasheng Wang, Dublin, OH (US); Jing-Ru Weng, Taichung (TW)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 12/118,591

(22) Filed: May 9, 2008

(65) Prior Publication Data

US 2008/0300291 A1 Dec. 4, 2008

Related U.S. Application Data

(60) Provisional application No. 60/938,899, filed on May 18, 2007.

(51) Int. Cl.
- A61K 31/404 (2006.01)
- A61P 35/00 (2006.01)
- C07D 209/14 (2006.01)

(52) U.S. Cl. .................. 514/415; 548/491
(58) Field of Classification Search ............ 548/452; 514/412
See application file for complete search history.

(56) References Cited

U.S. PATENT DOCUMENTS

| 6,800,655 B2 | 10/2004 | Jong et al. |
| 7,078,427 B2 | 7/2006 | Jong et al. |
| 2005/0043385 A1 | 2/2005 | Kiplin et al. |

FOREIGN PATENT DOCUMENTS

| GB | 1490671 | 11/1977 |
| WO | WO9850357 | 11/1998 |
| WO | WO2004048330 | 6/2004 |
| WO | WO2004055026 | 7/2004 |

OTHER PUBLICATIONS

Kondo et al, Heterocycles (1996), vol. 42(1), pp. 105-108, .http://www.heterocycles.jp/pfiles/pdf.php/COM-95-S31.pdf?article=6317.*
Kutschy, et al. Tetrahedron (1998), vol. 54, pp. 3549-3566.*
International Search Report for PCT/US08/63323; mailed Oct. 13, 2008.
Aggarwal et al., "Molecular targets and anticancer potential of indole-3-carbinol and its derivatives", Cell Cycle 4: p. 1201-1215 (2005).
Allen et al., "Entry into 6-methoxy-D(+)-tryptophans. Stereospecific synthesis of 1-benzenesulfonyl-6-methoxy-D(+)-tryptophan ethyl ester", Synthetic Communications, vol. 22, No. 14, p. 2077-2102 (1992).
Brandi et al., "A new indole-3-carbinol tetrameric derivative inhibits cyclin-dependent kinase 6 expression, and induces G1 cell cycle arrest in both estrogen-dependent and estrogen-independent breast cancer cell lines", Cancer Res. 63: p. 4028-4036 (2003).
Chinni et al., "Indole-3-carbinol (I3C) induced cell growth inhibition, G1 cell cycle arrest and apoptosis in prostate cancer cells", Oncogene 20: p. 2927-2936 (2001).
Chinni et al., "Akt inactivation is a key event in indole-3-carbinol-induced apoptosis in PC-3 cells", Clin Cancer Res. 8: p. 1228-1236 (2002).
Chintharlapalli et al., "1,1-Bis(3'-indolyl)-1-(p-substitutedphenyl) methanes induce peroxisome proliferator-activated receptor gamma-mediated growth inhibition, transactivation, and differentiation markers in colon cancer cells", Cancer Res. 64: p. 5994-6001 (2004).
Chintharlapalli et al., "1,1-Bis (3'-indolyl)-1-(p-substituted phenyl) methanes are peroxisome proliferator-activated receptor gamma agonists but decrease HCT-116 colon cancer cell survival through receptor-independent activation of early growth response-1 and nonsteroidal anti-inflammatory drug-activated gene-1", Mol Pharmacol 68: p. 1782-1792 (2005).
Contractor et al., "A novel ring-substituted diindolymethane, 1,1-bis[3'-(5-methoxyindolyl)]-1-(p-t-butylphenyl) methane, inhibits extracellular signal-regulated kinase activation and induces apoptosis in acute myelogenous leukemia", Cancer Res 65: p. 2890-2898 (2005).
De Kruif et al., "Structure elucidation of acid reaction products of indole-3-carbinol: detection in vivo and enzyme induction in vitro", Chem Biol Interact, 80: p. 303-315 (1991).

(Continued)

Primary Examiner—Kamal A Saeed
(74) Attorney, Agent, or Firm—Calfee, Halter & Griswold LLP

(57) ABSTRACT

Compounds and methods for treating cancer and inducing apoptosis in unwanted rapidly proliferating cells. The compounds are shown in formula I:

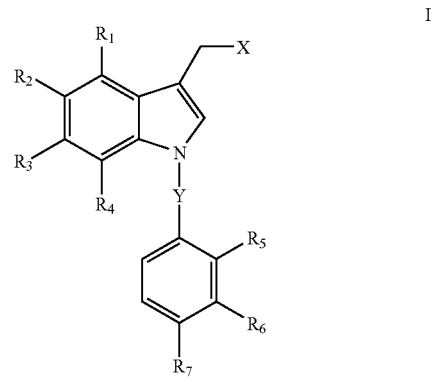

wherein X is hydroxyl or amino; Y is carboxyl or sulfonyl; $R_1$, $R_2$, $R_3$, and $R_4$ can be the same or different and are selected from hydrogen, halogen, methoxy, trifluoromethyl, hydroxyl and combinations thereof, $R_5$, $R_6$, and $R_7$ may be the same or different and are selected from hydrogen, chloro, bromo, nitro, phenyl, amino, methoxy, and combinations thereof, and derivatives or metabolites thereof.

19 Claims, 9 Drawing Sheets

OTHER PUBLICATIONS

Dropinski et al., "Synthesis and biological activities of novel aryl indole-2-carboxylic acid analogs as PPARgamma partial agonists", Bioorg Med Chem Lett 15: p. 5035-5038 (2005).

Gribble et al., "Syntheses and Diels-Alder cycloaddition reactions of 4H-furo[3,4-b] indoles. A regiospecific Diels-Alder synthesis of ellipticine", J of Organic Chemistry, vol. 57, No. 22 p. 5878-5891 (1992).

Grose et al., "Oligomerization of indole-3-carbinol in aqueous acid", Chem Res Toxicol 5: p. 188-193 (1992).

Henke et al., "Synthesis and biological activity of a novel series of indole-derived PPARgamma agonists", Bioorg Med Chem Lett 9: p. 3329-3334.

Howells et al., "Inhibition of phosphatidylinositol 3-kinase/protein kinase B signaling is not sufficient to account for indole-3-carbinol-induced apoptosis in some breast and prostate tumor cells", Clin Cancer Res 11: p. 8521-8527 (2005).

Hsu et al., "Indole-3-carbinol inhibition of androgen receptor expression and downregulation of androgen responsiveness in human prostate cancer cells", Carcinogenesis 26: p. 1896-1904 (2005).

Kassouf et al., "Inhibition of bladder tumor growth by 1,1-bis(3'-indolyl)-1-(p-substitutedphenyl) methanes: a new class of peroxisome proliferator-activated receptor gamma agonists", Cancer Res 66: p. 412-418 (2006).

Kim et al., "Targets for indole-3-carbinol in cancer prevention", J Nutr Biochem 16: p. 65-73 (2005).

Kutschy et al., "New Synthesis of Indole Phytoalexins and related compounds", Tetrahedron, vol. 54, No. 14, p. 3349-3566 (1998).

Manson, M., "Inhibition of survival signaling by dietary polyphenols and indole-3-carbinol", Eur. J Cancer 41: p. 1842-1853 (2005).

Nachshon-Kedmi et al., "Indole-3-carbinol and 3,3'-diindolylmethane induce apoptosis in human prostate cancer cells", Food Chem Toxicol 41: p. 745-752 (2003).

Qin et al., "A new class of peroxisome proliferator-activated receptor gamma (PPARgamma) agonists that inhibit growth of breast cancer cells: 1,1-Bis(3'-indolyl)-1-(p-substituted phenyl) methanes", Mol Cancer Ther., 3: p. 247-259 (2004).

Sarkar et al., "Indole-3-Carbinol and prostate cancer," J. Nutr., pp. 3493S-3498S (2004).

Weng et al., "A potent indole-3-carbinol-derived antitumor agent with pleiotropic effects on multiple signaling pathways in prostate cancer cells" Cancer Research vol. 67, No. 16 p. 7815-7824 (2007).

* cited by examiner

POTENT INDOLE-3-CARBINOL-DERIVED ANTITUMOR AGENTS

CROSS-REFERENCE TO RELATED APPLICATIONS

This application claims priority to U.S. Provisional Patent Application No. 60/938,899 filed May 18, 2007, the disclosure of which is incorporated herein by reference in its entirety.

STATEMENT REGARDING FEDERALLY FUNDED RESEARCH

This invention was made with government support under CA94829 awarded by the National Cancer Institute; CA112250 awarded by the National Cancer Institute; and W81XWH-05-1-0089 awarded by the Department of Defense. The government has certain rights in the invention.

BACKGROUND OF THE INVENTION

The chemopreventive potential of indole-3-carbinol, a naturally occurring phytochemical in cruciferous vegetables, has received much attention in light of its demonstrated in vivo efficacy to protect against chemical-induced carcinogenesis in animals. Moreover, the clinical benefits of indole-3-carbinol have also been demonstrated in human trials for cervical dysplasia, breast cancer, and vulvar intraepithelial neoplasia. Despite these advances in translational research, the mechanism by which indole-3-carbinol inhibits tumorigenesis remains inconclusive, which, in part, might be attributable to its metabolic instability and complicated pharmacological properties. The intrinsic instability of indole-3-carbinol in acidic milieu arises from the vinyl hemiaminal moiety of the indole ring. This unique structural feature underlies the high susceptibility of indole-3-carbinol to acid-catalyzed dehydration and condensation to generate a complicated series of oligomeric products in vivo, including DIM (3,3'-diindoylmethane), ICZ (indolo[3,2b]-carbazole), LTr$_1$ (a linear trimer), CTr (a cyclic trimer), and CTet (a cyclic tetramer). Similar to indole-3-carbinol, all these metabolites also exhibit inhibitory activities against tumor cell growth, however, with moderate to low potency.

Mechanistic evidence indicates that indole-3-carbinol facilitates growth arrest and apoptosis by targeting a broad range of signaling pathways pertinent to cell cycle regulation and survival, including those mediated by Akt, NF-κB, Bcl-2, mitogen-activated protein (MAP) kinases, the cyclin-dependent kinase (CDK) inhibitors p21 and p27, and cyclin D1. However, as these signaling targets often operate in a cell-specific fashion, it remains in dispute whether any of them could solely account for the effect of indole-3-carbinol on growth arrest and apoptosis in tumor cell. Furthermore, indole-3-carbinol and its metabolites suffer from metabolic instability, unpredictable pharmacokinetic properties, and low in vitro antiproliferative potency, which render therapeutic concentrations difficult to predict in the body.

Recent years have witnessed the use of DIM as a scaffold to carry out structural modifications, which has led to three distinct antitumor agents with higher potency: (p-substituted phenyl)-DIMs (PPARγ agonists), SR13668 (an Akt inhibitor), and an indole-3-carbinol tetrameric derivative (a CDK6 inhibitor). These novel agents exhibit μM potency in inducing apoptosis or cell cycle arrest, however, through signaling pathways distinct from that affected by DIM.

The present invention is directed to the use of indole-3-carbinol as a scaffold to carry out structural modifications in order to achieve antitumor agents that are distinct in comparison to native indole-3-carbinol and its metabolites, as well as DIM-based compounds.

SUMMARY OF THE INVENTION

The invention relates to compounds and methods for inducing apoptosis in unwanted rapidly proliferating cells. In one embodiment, the invention relates to novel indole-3-carbinol-derived antitumor agents that are structurally and mechanistically distinct from known derivates generated from indole-3-carbinol and DIM. The compounds of the present invention are shown in formula I:

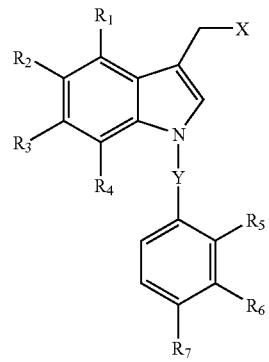

wherein X is hydroxyl or amino; Y is carboxyl or sulfonyl; $R_1$, $R_2$, $R_3$, and $R_4$ can be the same or different and are selected from hydrogen, halogen, methoxy, trifluoromethyl, hydroxyl and combinations thereof, $R_5$, $R_6$, and $R_7$ may be the same or different and are selected from hydrogen, chloro, bromo, nitro, phenyl, amino, methoxy, and combinations thereof, and derivatives or metabolites thereof.

In one embodiment, the invention relates to novel indole-3-carbinol-derived antitumor agents which exhibit the unique ability to target multiple molecular defects clinically relevant to oncogenesis and tumor progression, thereby providing an effective strategy for cancer therapy. In another embodiment, the invention relates to the use of [1-(3'-nitro-4'-chlorobenzenesulfonyl)-1H-indol-3-yl]-methanol, designated as OSU-A9, to target multiple pathways associated with oncogenesis and tumor progression. In another embodiment, the invention relates to methods of using OSU-A9 and other novel indole-3-carbinol derivatives for treating cancers, including but not limited to, prostate cancer, breast cancer, leukemia, non-small cell lung cancer, colon cancer, CNS cancer, melanoma, ovarian cancer, renal cancer, bladder cancer, and lymphoma.

DETAILED DESCRIPTION OF THE INVENTION

Figure 1A:
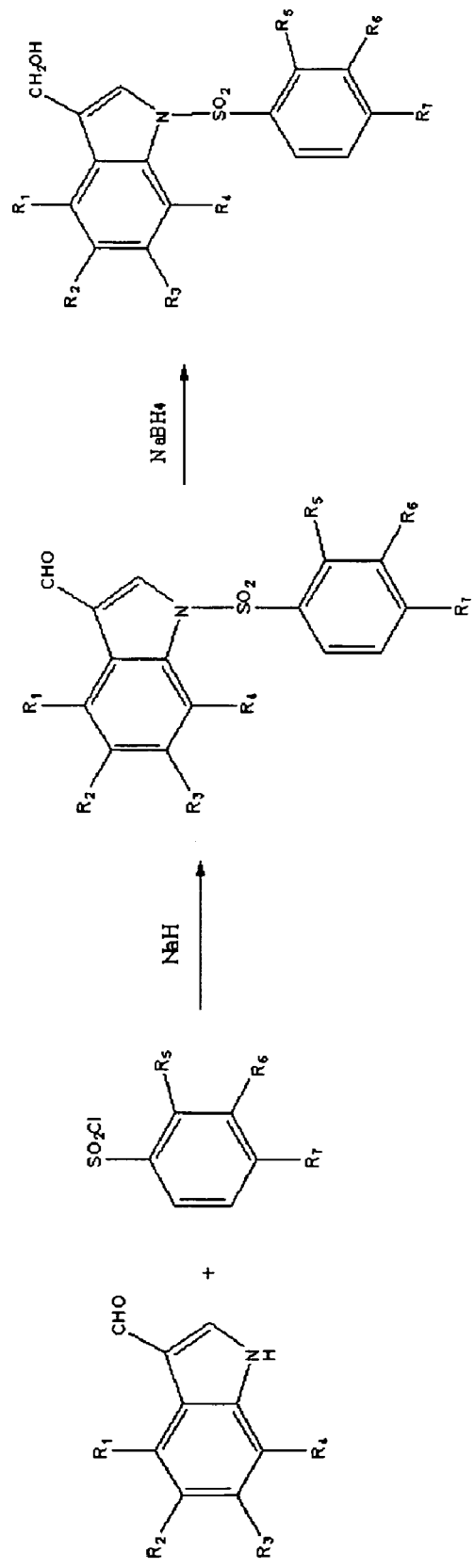
FIGS. 1 a-d show the synthetic schemes for preparing the compounds described herein.
Figure 1B:
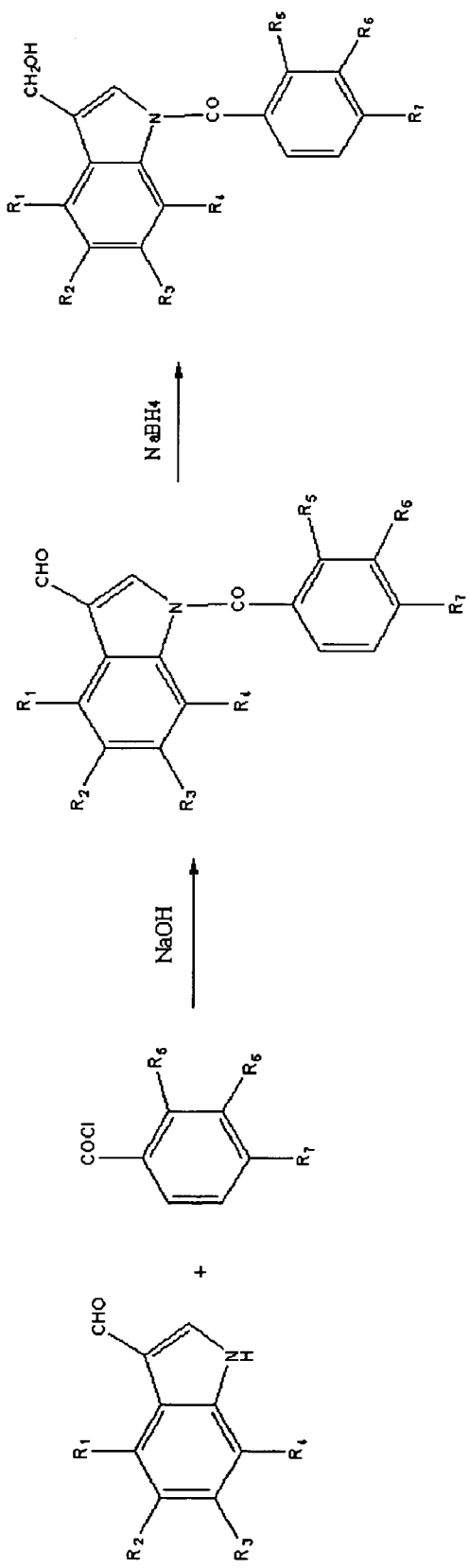
Figure 1C:
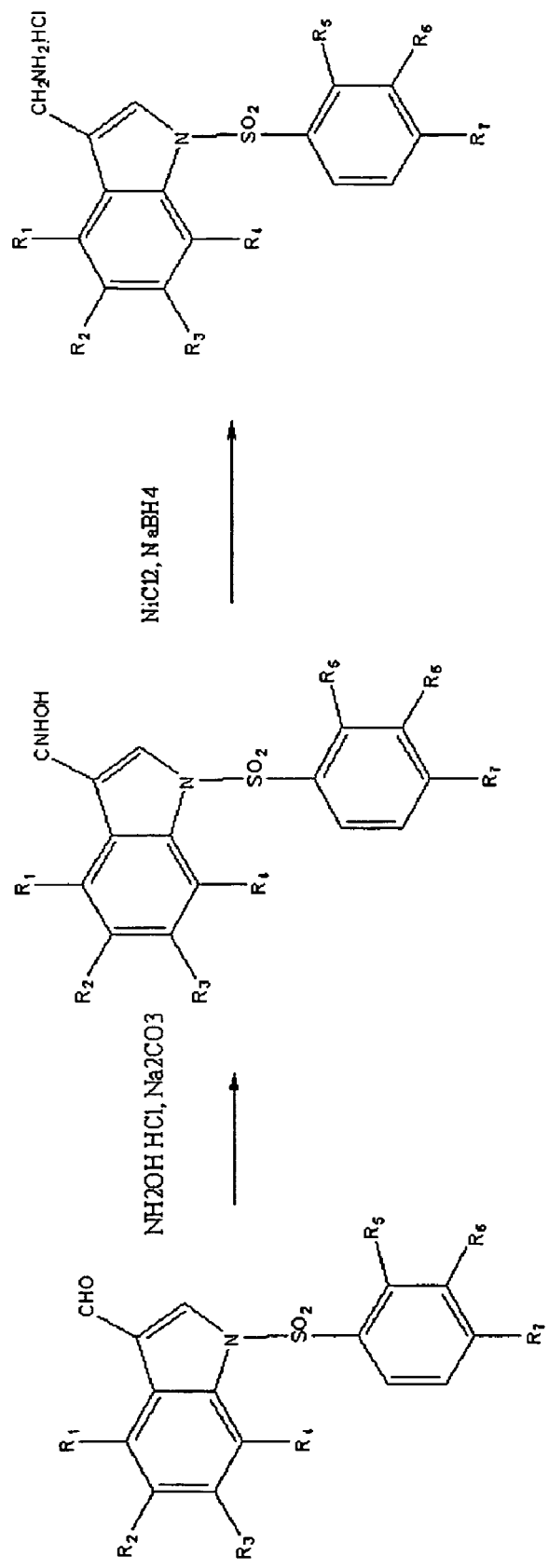
Figure 1D:
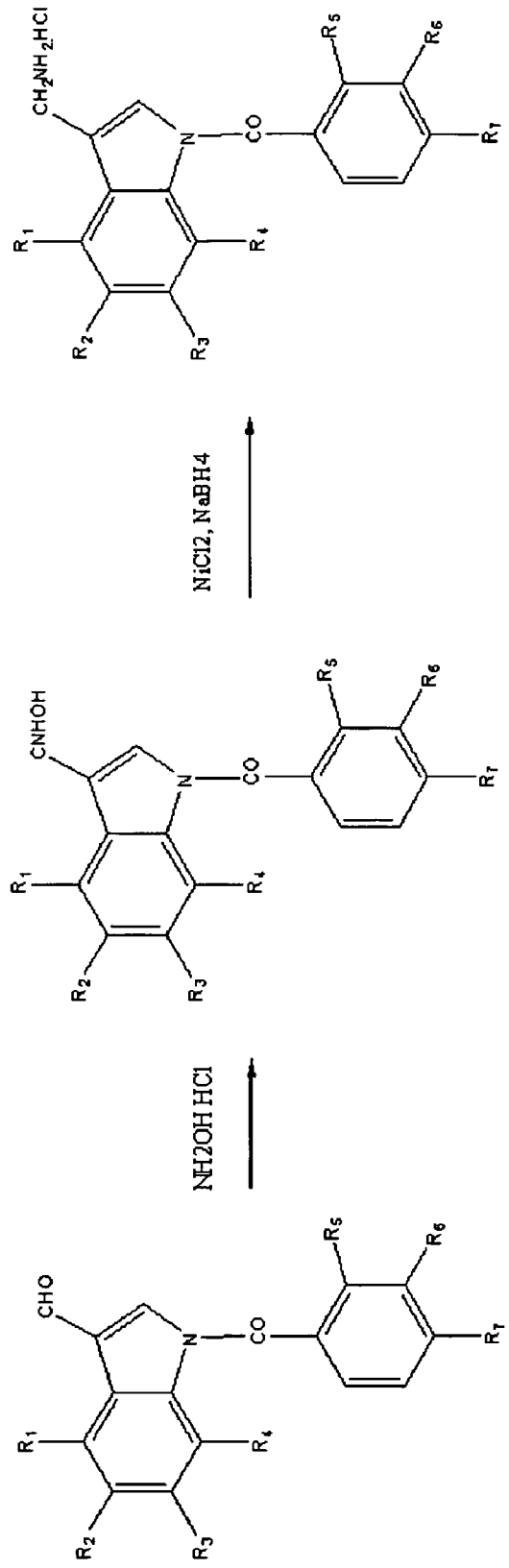

Described herein are compounds of formula I:

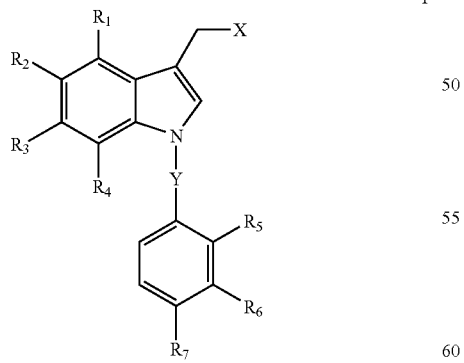

I wherein X is hydroxyl or amino; Y is carboxyl or sulfonyl; $R_1$, $R_2$, $R_3$, and $R_4$ can be the same or different and are selected from hydrogen, halogen, methoxy, trifluoromethyl, hydroxyl and combinations thereof, $R_5$, $R_6$, and $R_7$ may be the same or different and are selected from hydrogen, chloro, bromo, nitro, phenyl, amino, methoxy, and combinations thereof, and derivatives or metabolites thereof.

In one exemplary embodiment, $R_1$, $R_2$, $R_3$, and $R_4$ are hydrogen, X is hydroxyl, and Y is carboxyl. Some specific examples of this embodiment include:

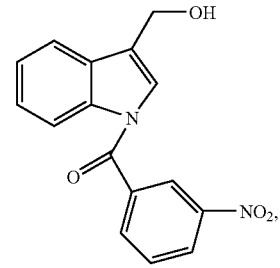

1-[(3'-nitrophenylcarboxyl)-1H-indol-3-yl] methanol

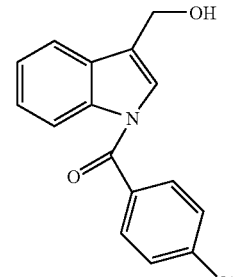

[1-(4'-chlorophenylcarboxyl)-1H-indol-3-yl] methanol

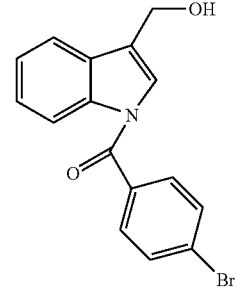

[1-(4'-bromophenylcarboxyl)-1H-indol-3-yl] methanol

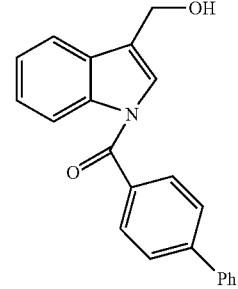

[1-(biphenylcarboxyl)-1H-indol-3-yl] methanol

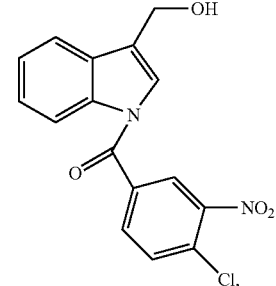

[1-(3'-nitro-4'-chlorophenylcarboxyl)-1H-indol-3-yl] methanol

-continued

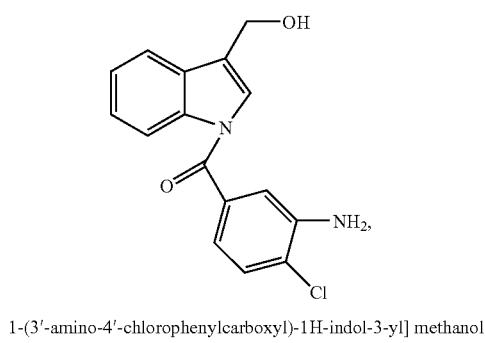

1-(3'-amino-4'-chlorophenylcarboxyl)-1H-indol-3-yl] methanol

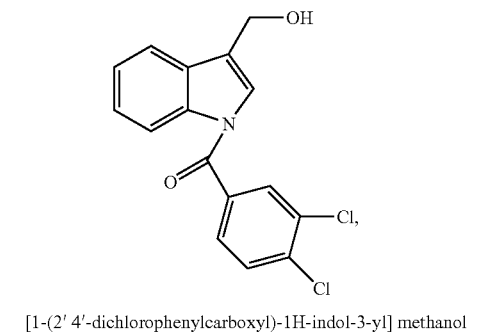

[1-(2' 4'-dichlorophenylcarboxyl)-1H-indol-3-yl] methanol

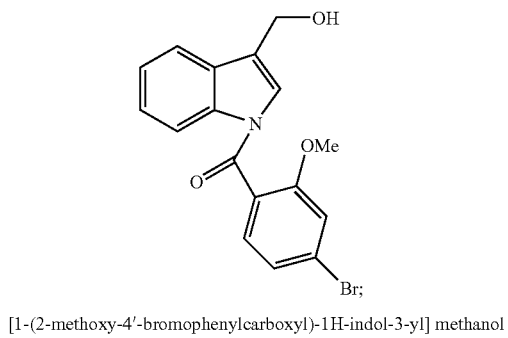

[1-(2-methoxy-4'-bromophenylcarboxyl)-1H-indol-3-yl] methanol and derivatives or metabolites thereof.

In another exemplary embodiment of the compound of formula I, $R_1$, $R_2$, $R_3$, and $R_4$ are hydrogen, X is hydroxyl, and Y is sulfonyl. Some specific examples of this embodiment include:

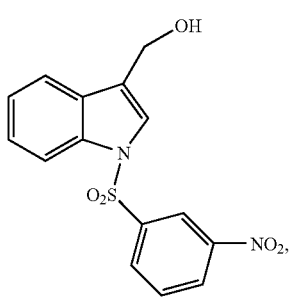

1-[(3'-nitrophenylsulfonyl)-1H-indol-3-yl] methanol

-continued

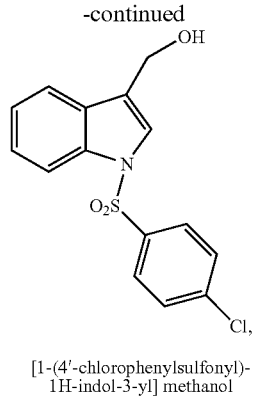

[1-(4'-chlorophenylsulfonyl)-1H-indol-3-yl] methanol

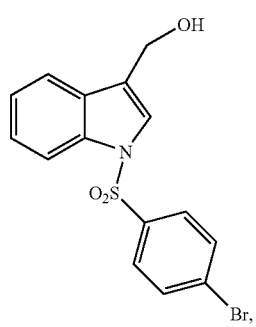

[1-(4'-bromophenylsulfonyl)-1H-indol-3-yl] methanol

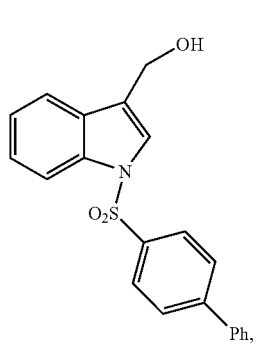

[1-(biphenylsulfonyl)-1H-indol-3-yl] methanol

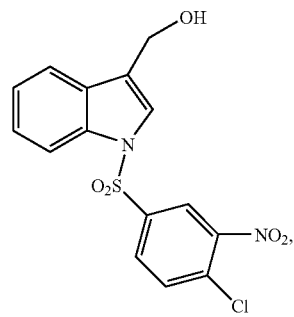

[1-(3'-nitro-4'-chlorophenylsulfonyl)-1H-indol-3-yl] methanol

-continued

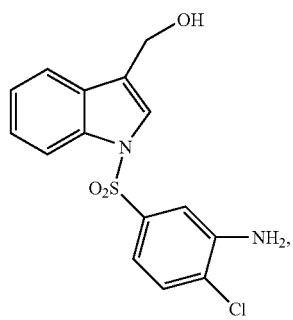

1-(3′-amino-4′-chlorophenylsulfonyl)-
1H-indol-3-yl] methanol

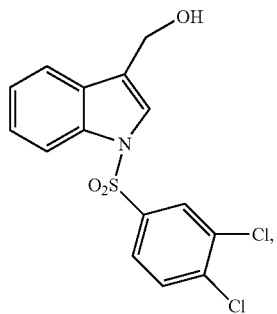

[1-(2′ 4′-dichlorophenylsulfonyl)-
1H-indol-3-yl] methanol

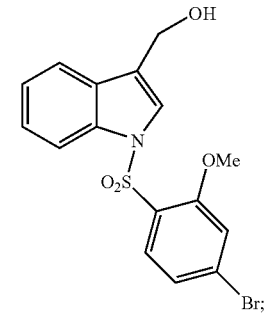

[1-(2′-methoxy-4′-bromophenylsulfonyl)-
1H-indol-3-yl] methanol and derivatives or metabolites thereof.

In another exemplary embodiment of the compound of formula I, $R_1$, $R_2$, $R_3$, and $R_4$ are hydrogen, X is amino, and Y is carboxyl. Some specific examples of this embodiment include:

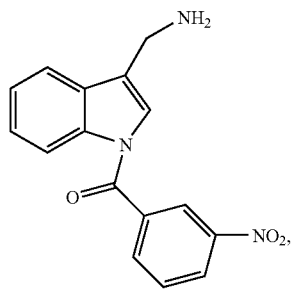

1-[(3′-nitrophenylcarboxyl)-
1H-indol-3-yl] methylamine

-continued

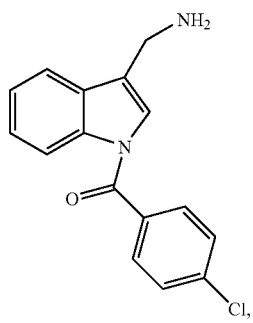

[1-(4′-chlorophenylcarboxyl)-
1H-indol-3-yl] methylamine

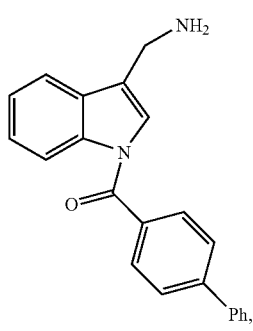

[1-(biphenylcarboxyl)-
1H-indol-3-yl] methylamine

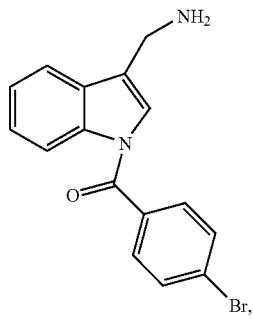

[1-(4′-bromophenylcarboxyl)-
1H-indol-3-yl] methylamine1

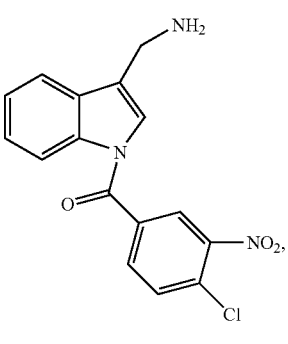

[1-(3′-nitro-4′-chlorophenylcarboxyl)-
1H-indol-3-yl] methylamine

-continued

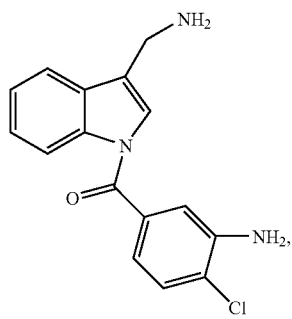

1-(3'-amino-4'-chlorophenylcarboxyl)-
1H-indol-3-yl] methylamine

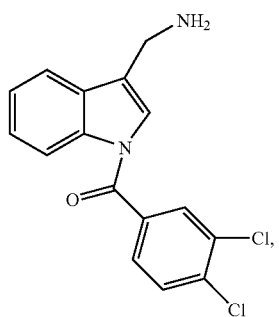

[1-(2' 4'-dichlorophenylcarboxyl)-
1H-indol-3-yl] methylamine

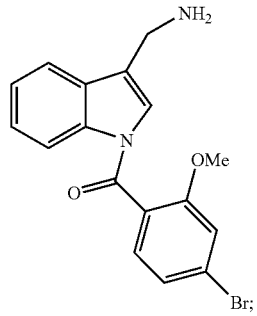

[1-(2'-methoxy-4'-bromophenylcarboxyl)-
1H-indol-3-yl] methylamine and derivatives or metabolites thereof.

In another specific embodiment, $R_1$, $R_2$, $R_3$, and $R_4$ are hydrogen, X is amino, and Y is sulfonyl. Some specific examples of this embodiment include:

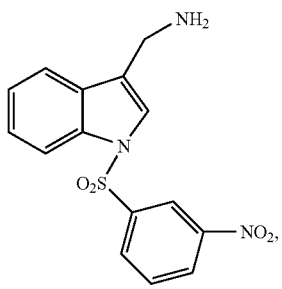

1-[(3'-nitrophenylsulfonyl)-1H-indol-3-yl] methylamine

-continued

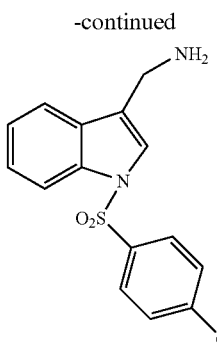

[1-(4'-chlorophenylsulfonyl)-1H-indol-3-yl] methylamine

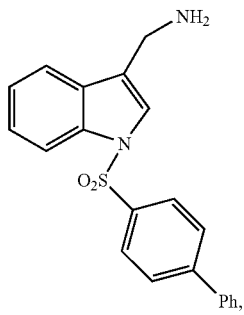

[1-(biphenylsulfonyl)-1H-indol-3-yl] methylamine

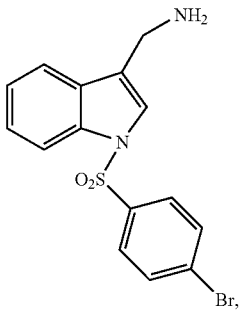

[1-(4'-bromophenylsulfonyl)-1H-indol-3-yl] methylamine

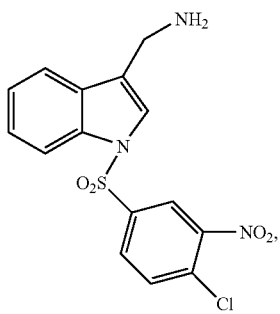

[1-(3'-nitro-4'-chlorophenylsulfonyl)-1H-indol-3-yl] methylamine

-continued

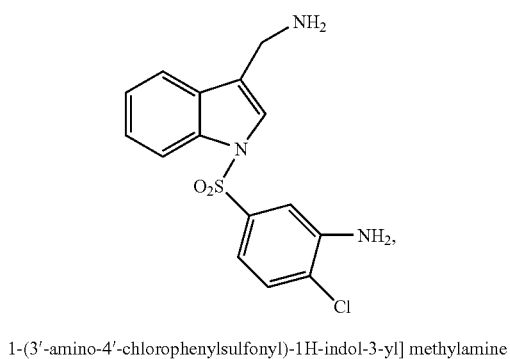

1-(3'-amino-4'-chlorophenylsulfonyl)-1H-indol-3-yl] methylamine

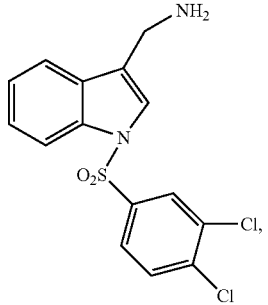

[1-(2' 4'-dichlorophenylsulfonyl)-1H-indol-3-yl] methylamine

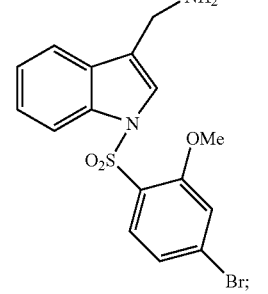

[1-(2'-methoxy-4'-bromophenylsulfonyl)-1H-indol-3-yl] methylamine and derivatives or metabolites thereof.

In another specific embodiment of the compound of formula I, $R_5$ is hydrogen, $R_6$ is nitro, $R_7$ is chloro, X is hydroxyl, and Y is carboxyl. Some specific examples of this embodiment include:

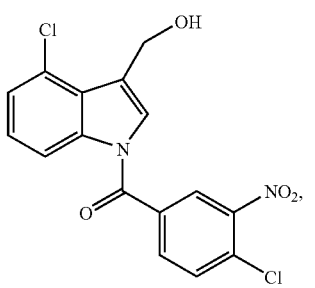

[1-(3'-nitro-4'-chlorophenylcarboxyl)-1H-5-chloro-indol-3-yl] methanol

-continued

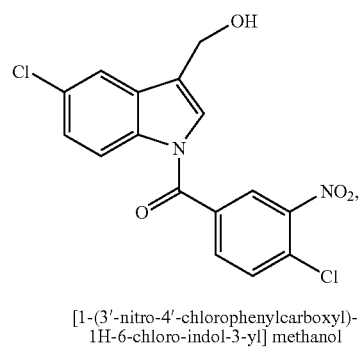

[1-(3'-nitro-4'-chlorophenylcarboxyl)-1H-6-chloro-indol-3-yl] methanol

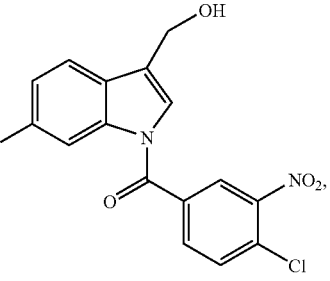

[1-(3'-nitro-4'-chlorophenylcarboxyl)-1H-7-chloro-indol-3-yl] methanol

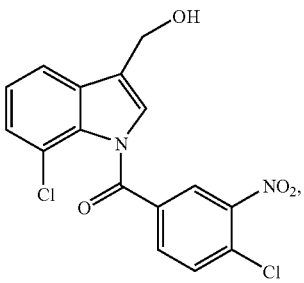

[1-(3'-nitro-4'-chlorophenylcarboxyl)-1H-8-chloro-indol-3-yl] methanol

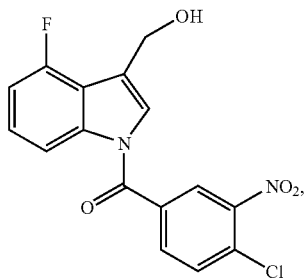

[1-(3'-nitro-4'-chlorophenylcarboxyl)-1H-5-fluoro-indol-3-yl] methanol

-continued

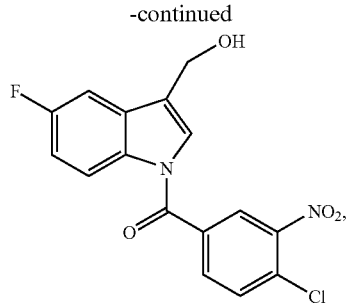

[1-(3′-nitro-4′-chlorophenylcarboxyl)-
1H-6-fluoro-indol-3-yl] methanol

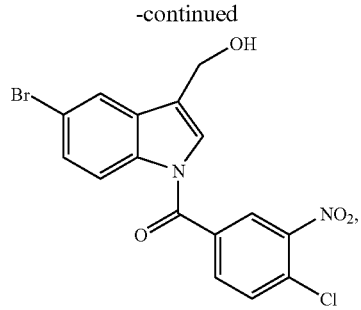

[1-(3′-nitro-4′-chlorophenylcarboxyl)-
1H-6-bromo-indol-3-yl] methanol

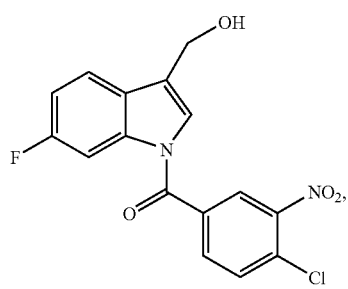

[1-(3′-nitro-4′-chlorophenylcarboxyl)-
1H-7-fluoro-indol-3-yl] methanol

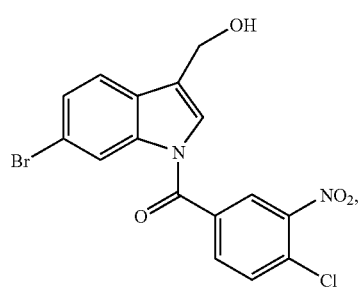

[1-(3′-nitro-4′-chlorophenylcarboxyl)-
1H-7-bromo-indol-3-yl] methanol

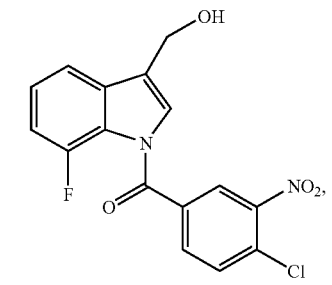

[1-(3′-nitro-4′-chlorophenylcarboxyl)-
1H-8-fluoro-indol-3-yl] methanol

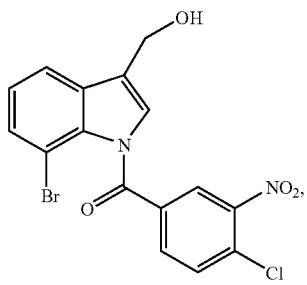

[1-(3′-nitro-4′-chlorophenylcarboxyl)-
1H-8-bromo-indol-3-yl] methanol

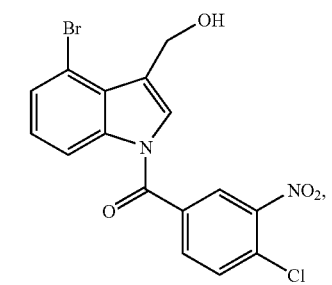

[1-(3′-nitro-4′-chlorophenylcarboxyl)-
1H-5-bromo-indol-3-yl] methanol

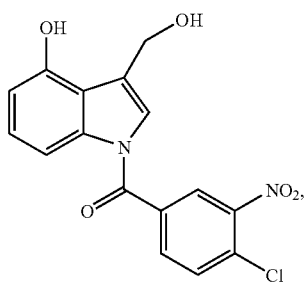

[1-(3′-nitro-4′-chlorophenylcarboxyl)-
1H-5-hydroxy-indol-3-yl] methanol

-continued

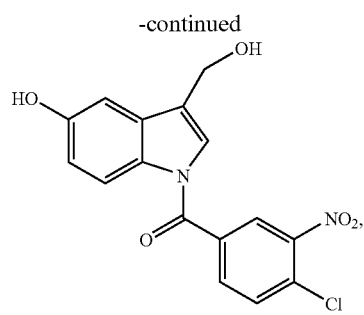

[1-(3'-nitro-4'-chlorophenylcarboxyl)-
1H-6-hydroxy-indol-3-yl] methanol

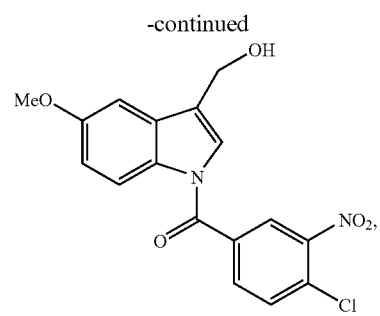

[1-(3'-nitro-4'-chlorophenylcarboxyl)-
1H-6-methoxy-indol-3-yl] methanol

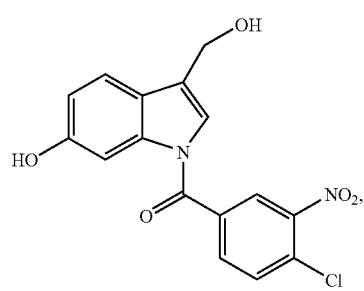

[1-(3'-nitro-4'-chlorophenylcarboxyl)-
1H-7-hydroxy-indol-3-yl] methanol

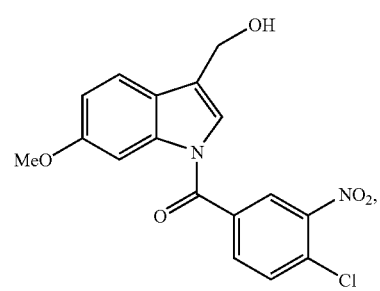

[1-(3'-nitro-4'-chlorophenylcarboxyl)-
1H-7-methoxy-indol-3-yl] methanol

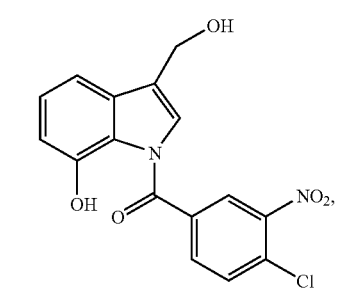

[1-(3'-nitro-4'-chlorophenylcarboxyl)-
1H-8-hydroxy-indol-3-yl] methanol

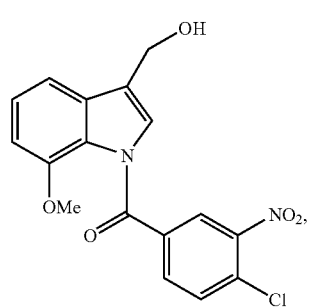

[1-(3'-nitro-4'-chlorophenylcarboxyl)-
1H-8-methoxy-indol-3-yl] methanol

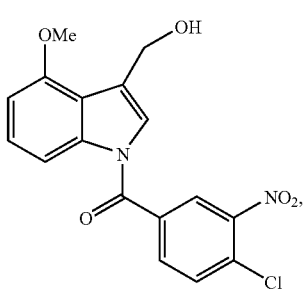

[1-(3'-nitro-4'-chlorophenylcarboxyl)-
1H-5-methoxy-indol-3-yl] methanol

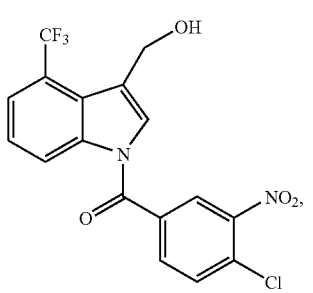

[1-(3'-nitro-4'-chlorophenylcarboxyl)-
1H-5-trifluoromethyl-indol-3-yl] methanol

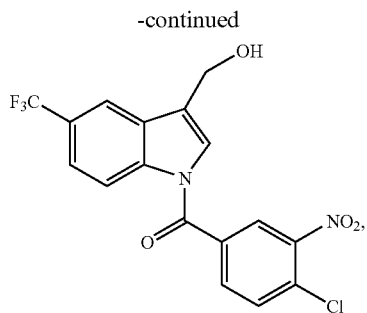

[1-(3'-nitro-4'-chlorophenylcarboxyl)-
1H-6-trifluoromethyl-indol-3-yl] methanol

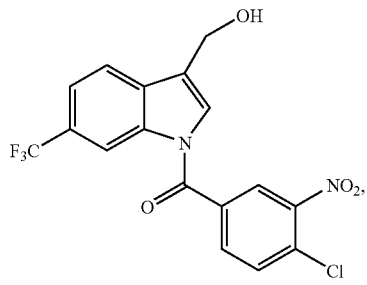

[1-(3'-nitro-4'-chlorophenylcarboxyl)-
1H-7-trifluoromethyl-indol-3-yl] methanol

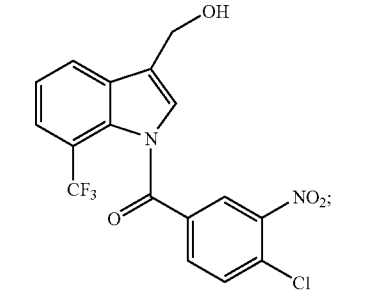

[1-(3'-nitro-4'-chlorophenylcarboxyl)-
1H-8-trifluoromethyl-indol-3-yl] methanol and derivatives or metabolites thereof.

In another specific embodiment of the compound of formula I, $R_5$ is hydrogen, $R_6$ is nitro, $R_7$ is chloro, X is hydroxyl, and Y is sulfonyl. Some specific examples of this embodiment include:

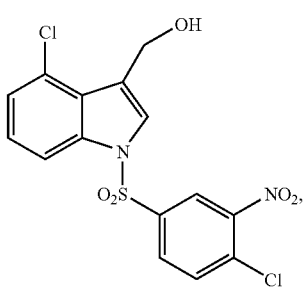

[1-(3'-nitro-4'-chlorophenylsulfonyl)-
1H-5-chloro-indol-3-yl] methanol

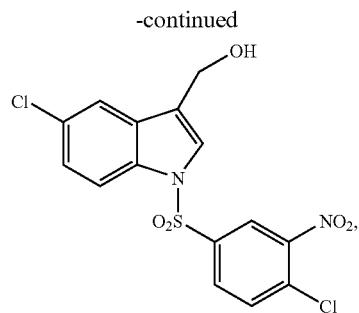

[1-(3'-nitro-4'-chlorophenylsulfonyl)-
1H-6-chloro-indol-3-yl] methanol

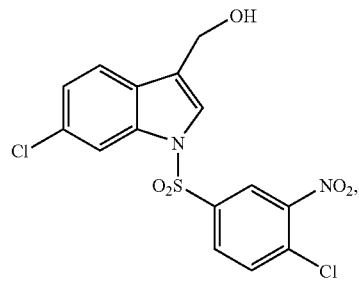

[1-(3'-nitro-4'-chlorophenylsulfonyl)-
1H-7-chloro-indol-3-yl] methanol

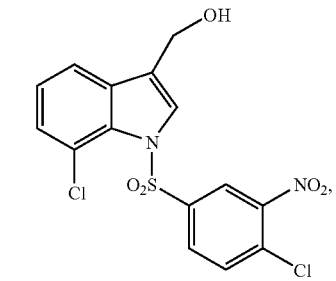

[1-(3'-nitro-4'-chlorophenylsulfonyl)-
1H-8-chloro-indol-3-yl] methanol

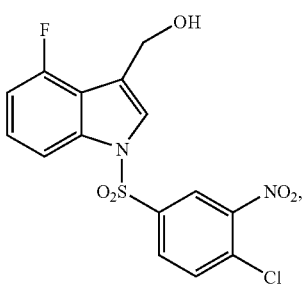

[1-(3'-nitro-4'-chlorophenylsulfonyl)-
1H-5-fluoro-indol-3-yl] methanol

-continued

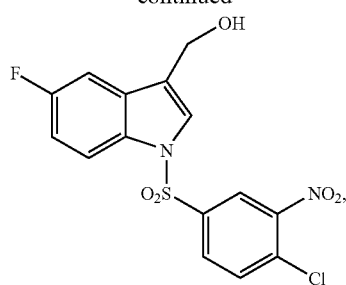

[1-(3'-nitro-4'-chlorophenylsulfonyl-1H-6-fluoro-indol-3-yl] methanol

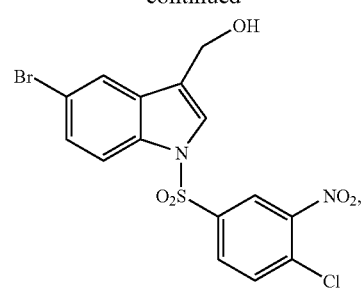

[1-(3'-nitro-4'-chlorophenylsulfonyl)-1H-6-bromo-indol-3-yl] methanol

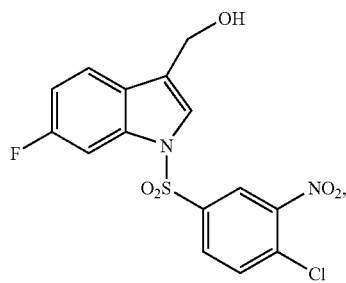

[1-(3'-nitro-4'-chlorophenylsulfonyl)-1H-7-fluoro-indol-3-yl] methanol

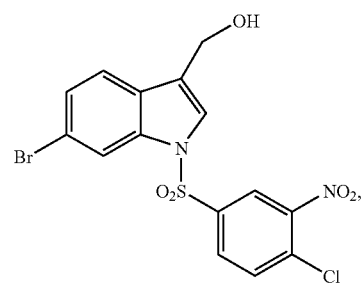

[1-(3'-nitro-4'-chlorophenylsulfonyl)-1H-7-bromo-indol-3-yl] methanol

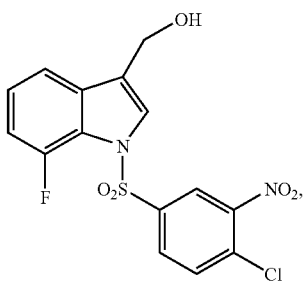

[1-(3'-nitro-4'-chlorophenylsulfonyl)-1H-8-fluoro-indol-3-yl] methanol

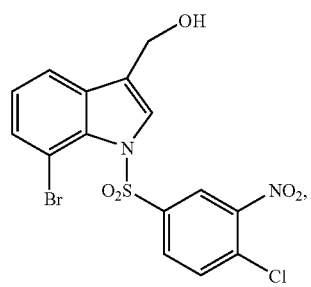

[1-(3'-nitro-4'-chlorophenylsulfonyl)-1H-8-bromo-indol-3-yl] methanol

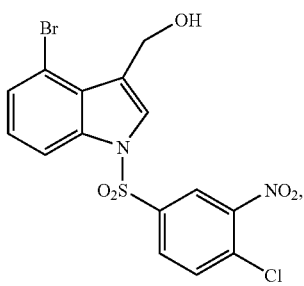

[1-(3'-nitro-4'-chlorophenylsulfonyl)-1H-5-bromo-indol-3-yl] methanol

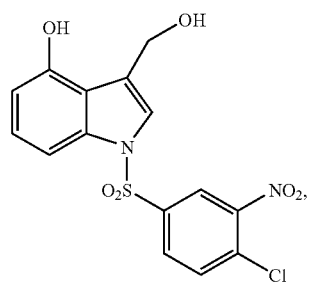

[1-(3'-nitro-4'-chlorophenylsulfonyl)-1H-5-hydroxy-indol-3-yl] methanol

-continued

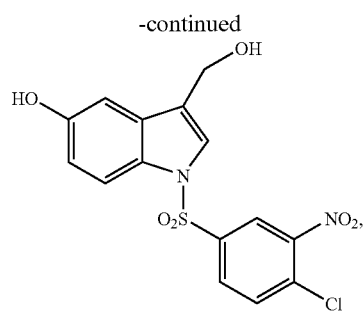

[1-(3'-nitro-4'-chlorophenylsulfonyl)-
1H-6-hydroxy-indol-3-yl] methanol

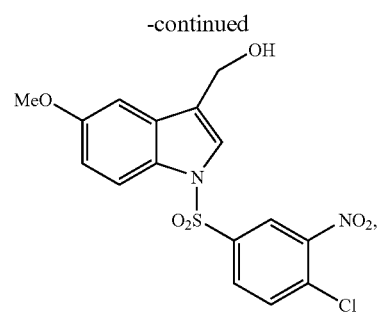

[1-(3'-nitro-4'-chlorophenylsulfonyl)-
1H-6-methoxy-indol-3-yl] methanol

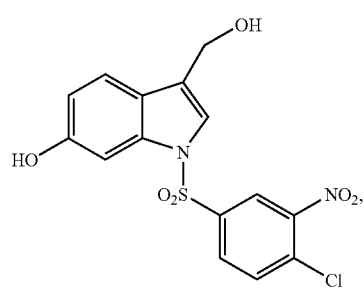

[1-(3'-nitro-4'-chlorophenylsulfonyl)-
1H-7-hydroxy-indol-3-yl] methanol

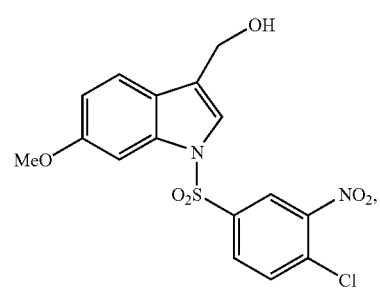

[1-(3'-nitro-4'-chlorophenylsulfonyl)-
1H-7-methoxy-indol-3-yl] methanol

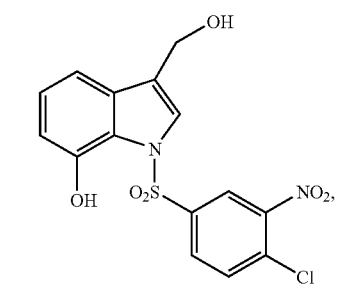

[1-(3'-nitro-4'-chlorophenylsulfonyl)-
1H-8-hydroxy-indol-3-yl] methanol

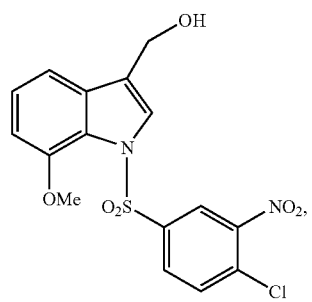

[1-(3'-nitro-4'-chlorophenylsulfonyl)-
1H-8-methoxy-indol-3-yl] methanol

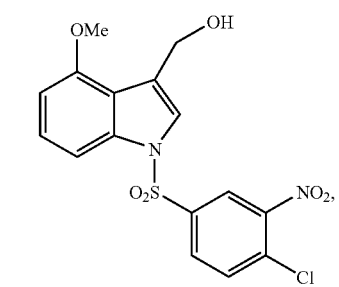

[1-(3'-nitro-4'-chlorophenylsulfonyl)-
1H-5-methoxy-indol-3-yl] methanol

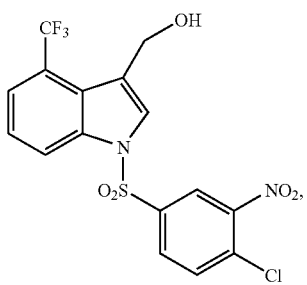

[1-(3'-nitro-4'-chlorophenylsulfonyl)-
1H-5-trifluoromethyl-indol-3-yl] methanol

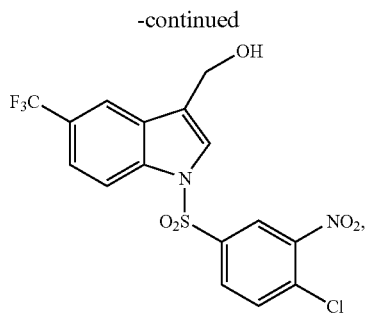

[1-(3'-nitro-4'-chlorophenylsulfonyl)-
1H-6-trifluoromethyl-indol-3-yl] methanol

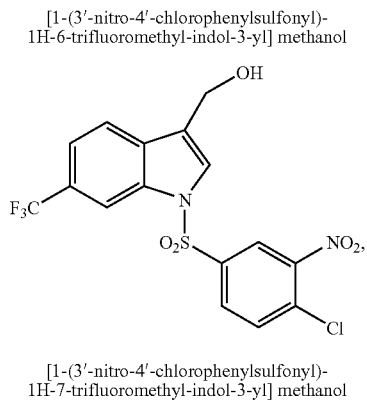

[1-(3'-nitro-4'-chlorophenylsulfonyl)-
1H-7-trifluoromethyl-indol-3-yl] methanol

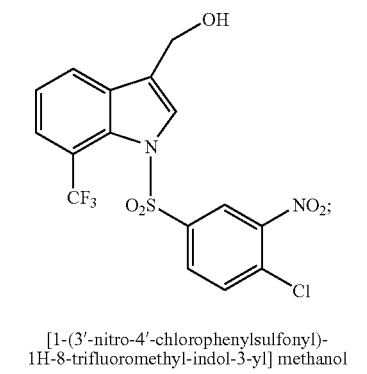

[1-(3'-nitro-4'-chlorophenylsulfonyl)-
1H-8-trifluoromethyl-indol-3-yl] methanol and derivatives or metabolites thereof.

In another embodiment, $R_5$ is hydrogen, $R_6$ is nitro, $R_7$ is chloro, X is amino, and Y is carboxyl. Some specific examples of this embodiment include:

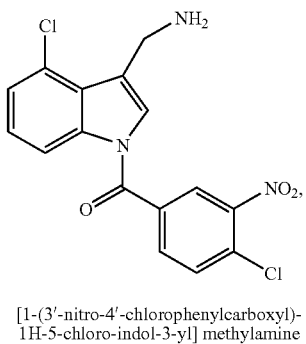

[1-(3'-nitro-4'-chlorophenylcarboxyl)-
1H-5-chloro-indol-3-yl] methylamine

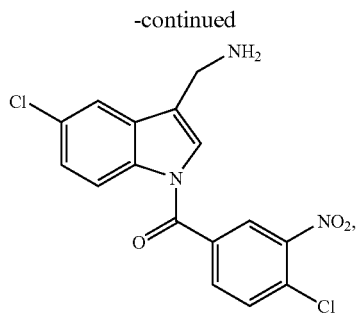

[1-(3'-nitro-4'-chlorophenylcarboxyl)-
1H-6-chloro-indol-3-yl] methylamine

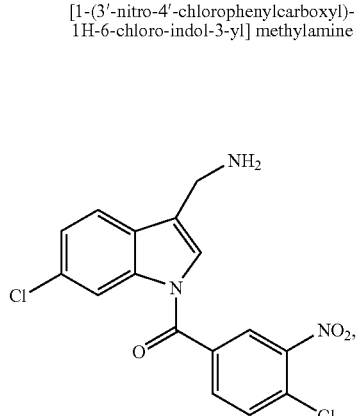

[1-(3'-nitro-4'-chlorophenylcarboxyl)-
1H-7-chloro-indol-3-yl] methylamine

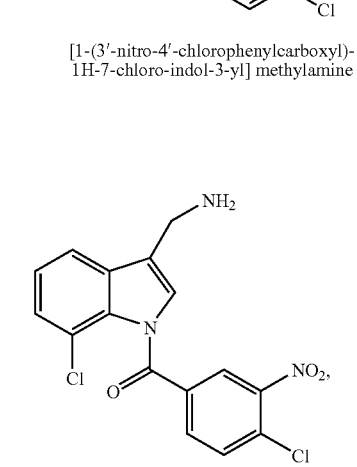

[1-(3'-nitro-4'-chlorophenylcarboxyl)-
1H-8-chloro-indol-3-yl] methylamine

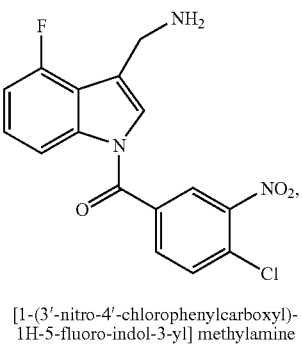

[1-(3'-nitro-4'-chlorophenylcarboxyl)-
1H-5-fluoro-indol-3-yl] methylamine

-continued

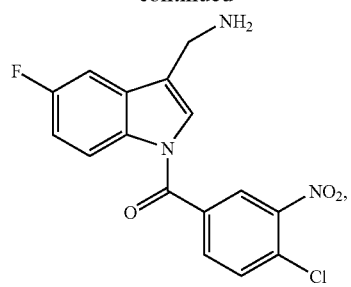

[1-(3'-nitro-4'-chlorophenylcarboxyl)-
1H-6-fluoro-indol-3-yl] methylamine

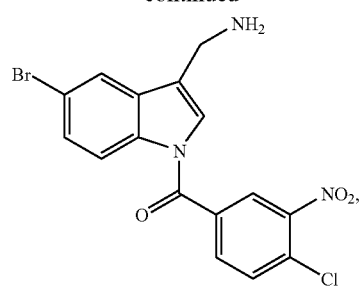

[1-(3'-nitro-4'-chlorophenylcarboxyl)-
1H-6-bromo-indol-3-yl] methylamine

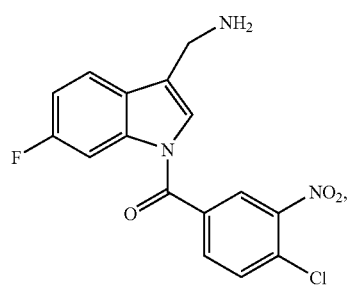

[1-(3'-nitro-4'-chlorophenylcarboxyl)-
1H-7-fluoro-indol-3-yl] methylamine

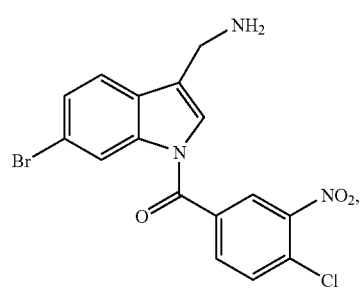

[1-(3'-nitro-4'-chlorophenylcarboxyl)-
1H-7-bromo-indol-3-yl] methylamine

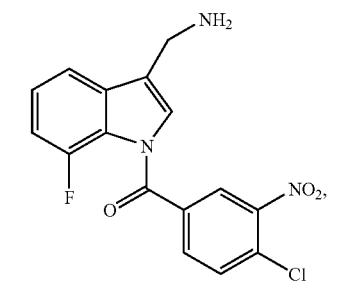

[1-(3'-nitro-4'-chlorophenylcarboxyl)-
1H-8-fluoro-indol-3-yl] methylamine

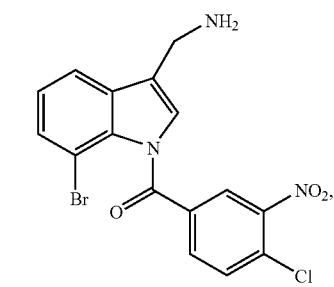

[1-(3'-nitro-4'-chlorophenylcarboxyl)-
1H-8-bromo-indol-3-yl] methylamine

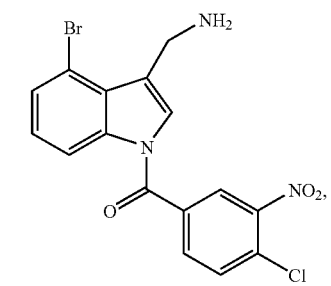

[1-(3'-nitro-4'-chlorophenylcarboxyl)-
1H-5-bromo-indol-3-yl] methylamine

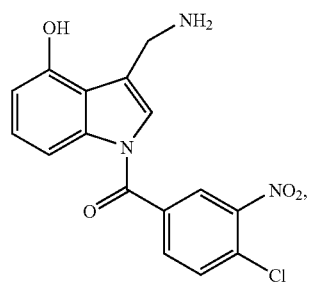

[1-(3'-nitro-4'-chlorophenylcarboxyl)-
1H-5-hydroxy-indol-3-yl] methylamine

-continued

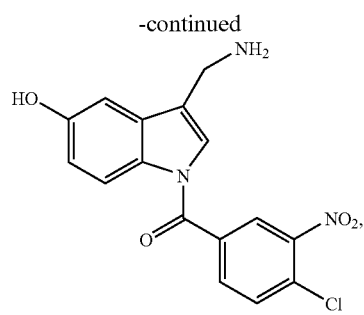

[1-(3'-nitro-4'-chlorophenylcarboxyl)-
1H-6-hydroxy-indol-3-yl] methylamine

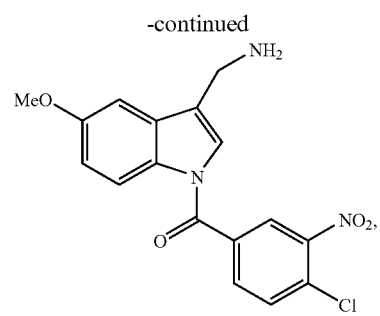

[1-(3'-nitro-4'-chlorophenylcarboxyl)-
1H-6-methoxy-indol-3-yl] methylamine

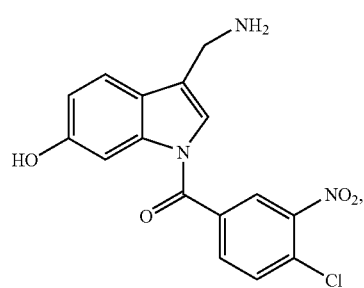

[1-(3'-nitro-4'-chlorophenylcarboxyl)-
1H-7-hydroxy-indol-3-yl] methylamine

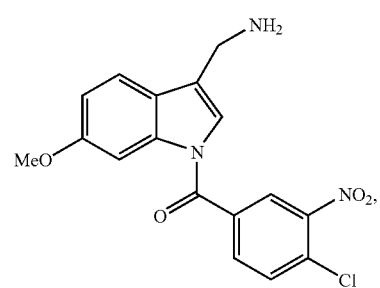

[1-(3'-nitro-4'-chlorophenylcarboxyl)-
1H-7-methoxy-indol-3-yl] methylamine

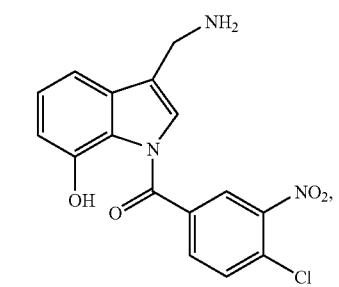

[1-(3'-nitro-4'-chlorophenylcarboxyl)-
1H-8-hydroxy-indol-3-yl] methylamine

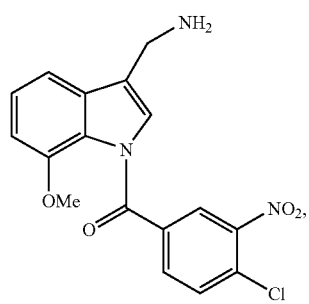

[1-(3'-nitro-4'-chlorophenylcarboxyl)-
1H-8-methoxy-indol-3-yl] methylamine

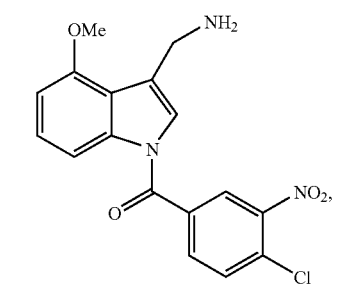

[1-(3'-nitro-4'-chlorophenylcarboxyl)-
1H-5-methoxy-indol-3-yl] methylamine

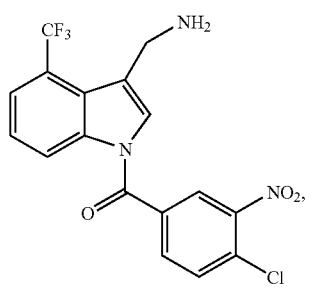

[1-(3'-nitro-4'-chlorophenylcarboxyl)-
1H-5-trifluoromethyl-indol-3-yl] methylamine

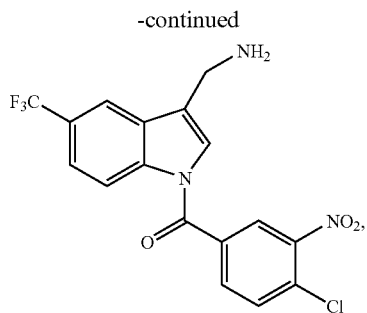

[1-(3'-nitro-4'-chlorophenylcarboxyl)-
1H-6-trifluoromethyl-indol-3-yl] methylamine

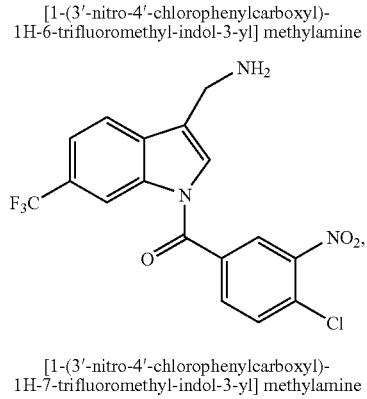

[1-(3'-nitro-4'-chlorophenylcarboxyl)-
1H-7-trifluoromethyl-indol-3-yl] methylamine

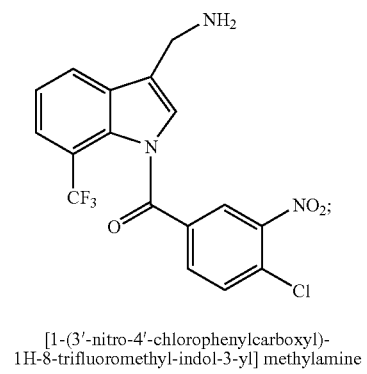

[1-(3'-nitro-4'-chlorophenylcarboxyl)-
1H-8-trifluoromethyl-indol-3-yl] methylamine and derivatives or metabolites thereof.

In another embodiment of formula I, $R_5$ is hydrogen, $R_6$ is nitro, $R_7$ is chloro, X is amino, and Y is sulfonyl. Some specific examples of this embodiment include:

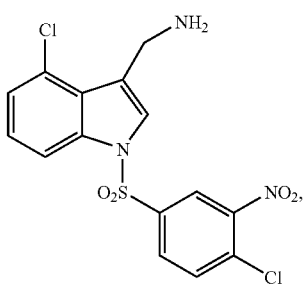

[1-(3'-nitro-4'-chlorophenylsulfonyl)-
1H-5-chloro-indol-3-yl] methylamine

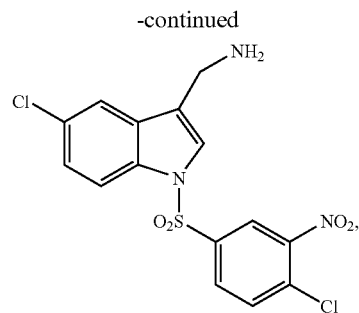

[1-(3'-nitro-4'-chlorophenylsulfonyl)-
1H-6-chloro-indol-3-yl] methylamine

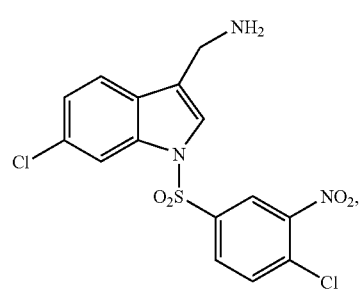

[1-(3'-nitro-4'-chlorophenylsulfonyl)-
1H-7-chloro-indol-3-yl] methylamine

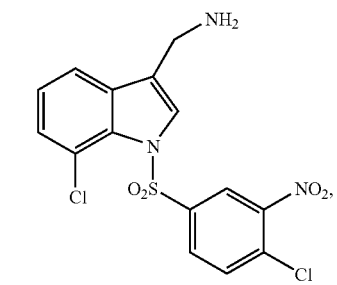

[1-(3'-nitro-4'-chlorophenylsulfonyl)-
1H-8-chloro-indol-3-yl] methylamine

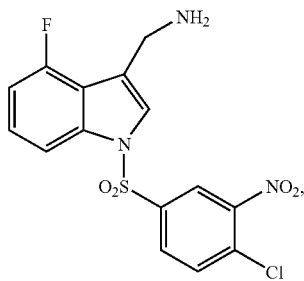

[1-(3'-nitro-4'-chlorophenylsulfonyl)-
1H-5-fluoro-indol-3-yl] methylamine

-continued

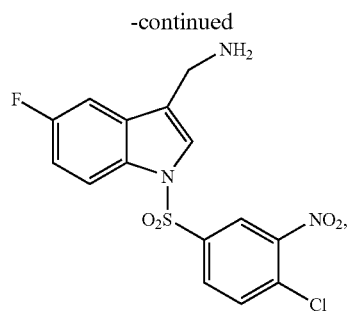

[1-(3′-nitro-4′-chlorophenylsulfonyl-
1H-6-fluoro-indol-3-yl] methylamine

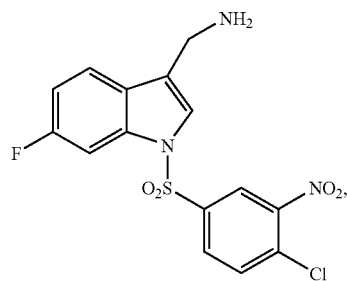

[1-(3′-nitro-4′-chlorophenylsulfonyl)-
1H-7-fluoro-indol-3-yl] methylamine

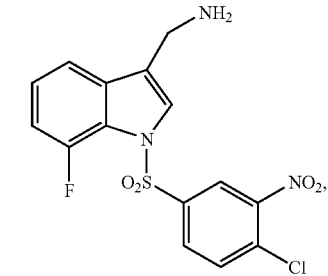

[1-(3′-nitro-4′-chlorophenylsulfonyl)-
1H-8-fluoro-indol-3-yl] methylamine

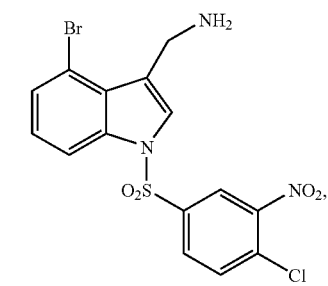

[1-(3′-nitro-4′-chlorophenylsulfonyl)-
1H-5-bromo-indol-3-yl] methylamine

-continued

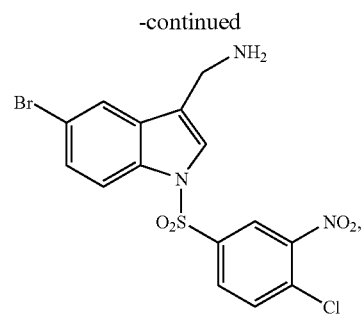

[1-(3′-nitro-4′-chlorophenylsulfonyl)-
1H-6-bromo-indol-3-yl] methylamine

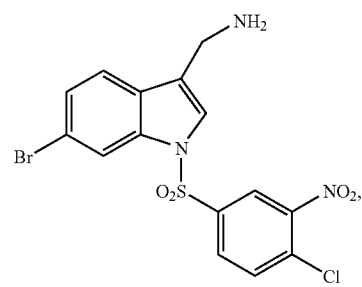

[1-(3′-nitro-4′-chlorophenylsulfonyl)-
1H-7-bromo-indol-3-yl] methylamine

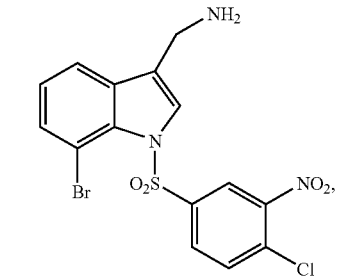

[1-(3′-nitro-4′-chlorophenylsulfonyl)-
1H-8-bromo-indol-3-yl] methylamine

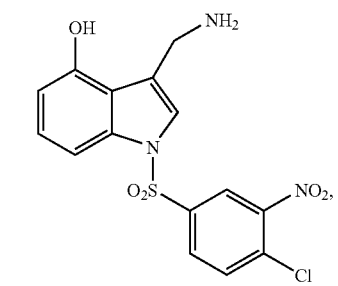

[1-(3′-nitro-4′-chlorophenylsulfonyl)-
1H-5-hydroxy-indol-3-yl] methylamine

-continued

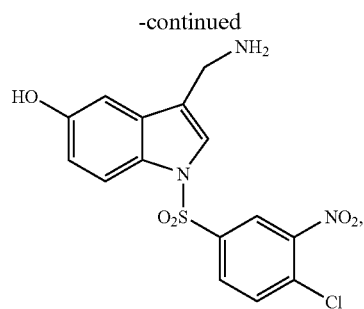

[1-(3'-nitro-4'-chlorophenylsulfonyl)-
1H-6-hydroxy-indol-3-yl] methylamine

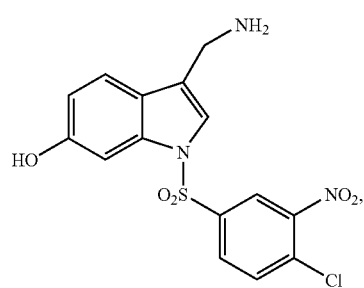

[1-(3'-nitro-4'-chlorophenylsulfonyl)-
1H-7-hydroxy-indol-3-yl] methylamine

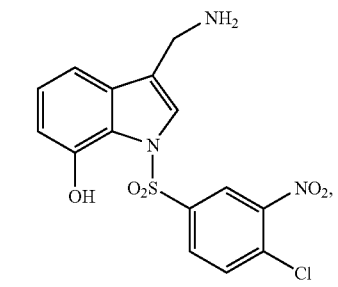

[1-(3'-nitro-4'-chlorophenylsulfonyl)-
1H-8-hydroxy-indol-3-yl] methylamine

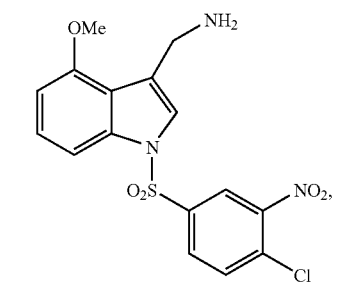

[1-(3'-nitro-4'-chlorophenylsulfonyl)-
1H-5-methoxy-indol-3-yl] methylamine

-continued

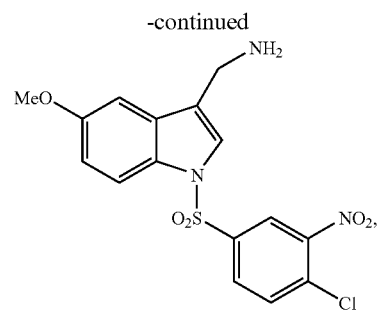

[1-(3'-nitro-4'-chlorophenylsulfonyl)-
1H-6-methoxy-indol-3-yl] methylamine

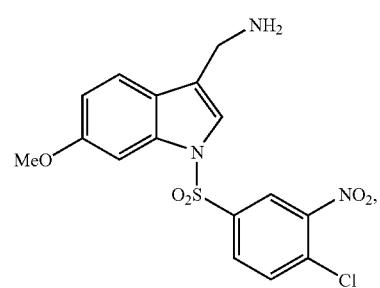

[1-(3'-nitro-4'-chlorophenylsulfonyl)-
1H-7-methoxy-indol-3-yl] methylamine

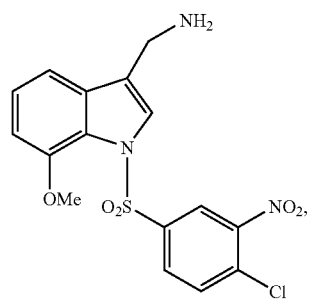

[1-(3'-nitro-4'-chlorophenylsulfonyl)-
1H-8-methoxy-indol-3-yl] methylamine

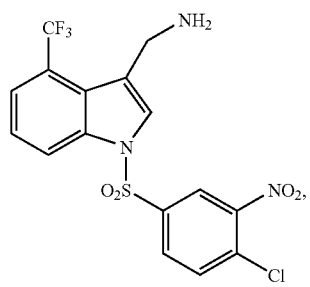

[1-(3'-nitro-4'-chlorophenylsulfonyl)-
1H-5-trifluoromethyl-indol-3-yl] methylamine

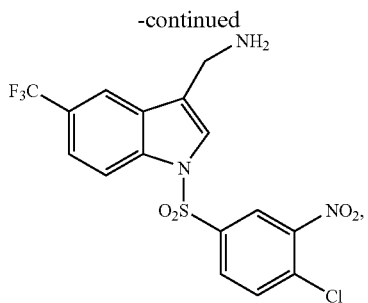

[1-(3'-nitro-4'-chlorophenylsulfonyl)-
1H-6-trifluoromethyl-indol-3-yl] methylamine

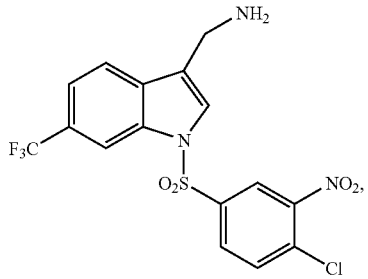

[1-(3'-nitro-4'-chlorophenylsulfonyl)-
1H-7-trifluoromethyl-indol-3-yl] methylamine

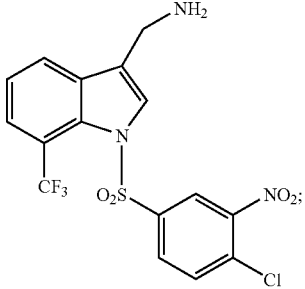

[1-(3'-nitro-4'-chlorophenylsulfonyl)-
1H-8-trifluoromethyl-indol-3-yl] methylamine and derivatives or metabolites thereof.

The compounds of formula I are useful in inducing apoptosis in proliferative cells, including, but not limited to cancer cells. The compounds are further useful for treating, inhibiting, and delaying the onset of cancer in mammals, and especially in humans. Cancers that these compounds work particularly well against include, but are not limited to prostate cancer, breast cancer, leukemia, non-small cell lung cancer, colon cancer, CNS cancer, melanoma, ovarian cancer, renal cancer, bladder cancer, lymphoma, and breast cancer. Surprisingly, the compounds of the present invention are able to induce apoptosis in cancer cells independent of the level of Bcl-2 expression and p53 functional status, which means that the inventive compounds are potent even against cancers that are androgen-independent, such as hormone-refractory prostate cancer.

Also provided are methods of using the compounds of formula I to treat, to prevent, or to delay the onset of disorders characterized by unwanted, rapid cell proliferation, including but not limited to cancer. The present invention also relates methods of using the inventive compounds to treat specific kinds of cancers, including but not limited to prostate cancer, breast cancer, leukemia, non-small cell lung cancer, colon cancer, CNS cancer, melanoma, ovarian cancer, renal cancer, bladder cancer, lymphoma, and breast cancer. Further provided are methods of treating, preventing, and delaying the onset of androgen-independent cancers, including methods of treating advanced prostate cancer.

The compounds and methods described herein are useful for, but not limited to treating, inhibiting, or delaying the onset of cancers. The compounds and methods are also useful in the treatment of precancers and other incidents of undesirable cell proliferation. The compounds of formula I may be administered to a subject experiencing undesirable cell proliferation. Furthermore, they are useful in the prevention of these cancers in individuals with precancers, as well as individuals prone to these disorders by administration of the compounds of formula I to these individuals.

The term "treatment" as used herein includes partial or total destruction of the undesirable proliferating cells with minimal destructive effects on normal cells. A desired mechanism of treatment at the cellular level is apoptosis.

The term "prevention" includes either preventing the onset of a clinically evident unwanted cell proliferation altogether or preventing the onset of a preclinically evident stage of unwanted rapid cell proliferation in individuals at risk. Also intended to be encompassed by this definition is the prevention of metastasis of malignant cells or to arrest or reverse the progression of malignant cells. This includes prophylactic treatment of those at risk of developing precancers and cancers.

The terms "therapeutically effective" and "pharmacologically effective" are intended to qualify the amount of each agent which will achieve the goal of improvement in disease severity and the frequency of incidence, while avoiding adverse side effects typically associated with alternative therapies.

The term "subject" for purposes of treatment includes any human or animal subject who has a disorder characterized by unwanted, rapid cell proliferation or is at risk of developing such a disorder. Such disorders include, but are not limited to cancers and precancers. For methods described herein, the subject is any human or animal subject, and in some embodiments, the subject is a human subject who has developed or is at risk of developing a disorder characterized by unwanted, rapid cell proliferation, such as cancer. The subject may be at risk due to exposure to carcinogenic agents, being genetically predisposed to disorders characterized by unwanted, rapid cell proliferation, and so on. Besides being useful for human treatment, the compounds of the present invention are also useful for veterinary treatment of mammals, including companion animals and farm animals, such as, but not limited to dogs, cats, horses, cows, sheep, and pigs.

The compounds of the present invention may trigger cell death by a number of different mechanisms, however, an aspect of the inventive compounds is that they are able to induce apoptosis in unwanted, proliferative cells. The term "apoptosis" refers to the process of programmed cell death. In every person hundreds of thousands of old or damaged cells die each day by the process of apoptosis and are replaced in the ebb and flow of maintaining a constant number of living cells in the body. Old and damaged cells die in response to a signal triggered on the cell surface for the targeted cell to self destruct. Apoptosis is distinguished from other mechanisms of cell death, such as necrosis, which results in inflammation including swelling, redness, pain and tenderness. Apoptosis does not stimulate such reactions. In apoptosis, the cells shrivel up, break into pieces and the contents are quietly removed by methods that do not induce inflammation. For these reasons, it is highly desirable to induce apoptosis, rather than necrosis, in rapidly proliferating cells, such as cancer cells. However, mutations in some cancer cells confer resistance of these cells to apoptosis. The compounds described herein have been found to induce apoptosis even in cancer cells which, because of mutations, are otherwise resistant to apoptosis. Apoptosis can be distinguished from other treatment mechanisms by methods such as microscopy, which are known in the art.

The terms "proliferative cells," "proliferating cells," "rapidly proliferating cells," "undesirable proliferating cells," "undesirable rapidly proliferating cells," "unwanted rapidly proliferating cells," and the like, refer to cancer cells, precancer cells, and other abnormal, rapidly dividing cells in a subject.

Derivatives are intended to encompass any compounds which are structurally related to the compounds of formula I which possess the substantially equivalent activity, as measured by the derivative's ability to induce apoptosis in rapidly proliferating cells without substantial COX-2 inhibition. By way of example, such compounds may include, but are not limited to, prodrugs thereof. Such compounds can be formed in vivo, such as by metabolic mechanisms.

Also described herein are therapeutic methods of inducing apoptosis in undesirable rapidly proliferating cells, which include, but are not limited to cancer cells. The methods comprise administering a therapeutically effective amount of a compound of formula I to a subject having a disorder or being predisposed to a disorder involving rapidly proliferating cells.

Where the term alkyl is used, either alone or with other terms, such as haloalkyl or alkylaryl, it includes $C_1$ to $C_{10}$ linear or branched alkyl radicals, examples include methyl, ethyl, propyl, isopropyl, butyl, tert-butyl, and so forth. The term "haloalkyl" includes $C_1$ to $C_{10}$ linear or branched alkyl radicals substituted with one or more halo radicals. Some examples of haloalkyl radicals include trifluoromethyl, 1,2-dichloroethyl, 3-bromopropyl, and so forth. The term "halo" includes radicals selected from F, Cl, Br, and I. Alkyl radical substituents of the present invention may also be substituted with other groups such as azido, for example, azidomethyl, 2-azidoethyl, 3-azidopropyl and so on.

The term aryl, used alone or in combination with other terms such as alkylaryl, haloaryl, or haloalkylaryl, includes such aromatic radicals as phenyl, biphenyl, and benzyl, as well as fused aryl radicals such as naphthyl, anthryl, phenanthrenyl, fluorenyl, and indenyl and so forth. The term "aryl" also encompasses "heteroaryls," which are aryls that have carbon and one or more heteroatoms, such as O, N, or S in the aromatic ring. Examples of heteroaryls include indolyl, pyrrolyl, and so on. "Alkylaryl" or "arylalkyl" refers to alkyl-substituted aryl groups such as butylphenyl, propylphenyl, ethylphenyl, methylphenyl, 3,5-dimethylphenyl, tert-butylphenyl and so forth. "Haloaryl" refers to aryl radicals in which one or more substitutable positions has been substituted with a halo radical, examples include fluorophenyl, 4 chlorophenyl, 2,5 chlorophenyl and so forth. "Haloalkylaryl" refers to aryl radicals that have a haloalkyl substituent. Examples of haloalkylaryls include such radicals as bromomethylphenyl, 4-bromobutylphenyl and so on. Carboxyamide refers to the group $CONH_2$, and sulfonamide refers to the group $SO_2NH_2$.

Also included in the family of compounds of formula I are the pharmaceutically acceptable salts thereof. The phrase "pharmaceutically acceptable salts" connotes salts commonly used to form alkali metal salts and to form addition salts of free acids or free bases. The nature of the salt is not critical, provided that it is pharmaceutically acceptable. Suitable pharmaceutically acceptable acid addition salts of compounds of formula I may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, galactaric, and galacturonic acids. Suitable pharmaceutically acceptable base addition salts of compounds of formula I include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the compounds of formula I. All of these salts may be prepared by conventional means from the corresponding compounds of formula I by reacting, for example, the appropriate acid or base with the compound of formula I.

The present invention further embodies a pharmaceutical composition for inducing apoptosis in undesirable, rapidly proliferating cells, such as for treating, preventing, or delaying the onset of a cancer in a subject in need of such treatment. The pharmaceutical composition comprises a therapeutically effective amount of a compound of formula I or a derivative or pharmaceutically acceptable salt thereof, in association with at least one pharmaceutically acceptable carrier, adjuvant, or diluent (collectively referred to herein as "carrier materials") and, if desired, other active ingredients. The active compounds of the present invention may be administered by any suitable route known to those skilled in the art, in the form of a pharmaceutical composition adapted to such a route, and in a dose effective for the treatment intended. The active compounds and composition may, for example, be administered orally, intra-vascularly, intraperitoneally, intranasally, intrabronchially, subcutaneously, intramuscularly or topically (including aerosol). With some subjects local administration, rather than system administration, may be more appropriate. Formulation in a lipid vehicle may be used to enhance bioavailability.

The administration of the present invention may be for either prevention or treatment purposes. The methods and compositions used herein may be used alone or in conjunction with additional therapies known to those skilled in the art in the prevention or treatment of disorders characterized by unwanted, rapid proliferation of cells. Alternatively, the methods and compositions described herein may be used as adjunct therapy. By way of example, the apoptosis-inducing compounds of the present invention may be administered alone or in conjunction with other antineoplastic agents or other growth inhibiting agents or other drugs or nutrients.

There are large numbers of antineoplastic agents available in commercial use, in clinical evaluation and in pre-clinical development, which could be selected for treatment of cancers or other disorders characterized by rapid proliferation of cells by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplastic agents, such as metallomatrix proteases inhibitors (MMP), such as MMP-13 inhibitors including batiastat, marimastat, Agouron Pharmaceuticals AG-3340, and Roche RO-32-3555, or $\alpha_v\beta_3$ inhibitors may be used. Suitable agents which may be used in combination therapy will be recognized by those of skill in the art. Similarly, when combination therapy is desired, radioprotective agents known to those of skill in the art may also be used.

The phrase "adjunct therapy" (or "combination therapy"), in defining use of a compound of the present invention and one or more other pharmaceutical agent, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

For oral administration, the pharmaceutical composition may be in the form of, for example, a tablet, capsule, suspension or liquid. In some embodiments, the pharmaceutical composition is made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is, in some embodiments, isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

If the unwanted proliferating cells are localized in the G.I. tract, the compound may be formulated with acid-stable, base-labile coatings known in the art which begin to dissolve in the high pH small intestine. In some exemplary embodiments, the compound is formulated to enhance local pharmacologic effects and reduce systemic uptake.

Formulations suitable for parenteral administration conveniently comprise a sterile aqueous preparation of the active compound which, in some embodiments, isotonic. Preparations for injections may also be formulated by suspending or emulsifying the compounds in non-aqueous solvent, such as vegetable oil, synthetic aliphatic acid glycerides, esters of higher aliphatic acids or propylene glycol.

Formulations for topical use include known gels, creams, oils, and the like. For aerosol delivery, the compounds may be formulated with known aerosol exipients, such as saline, and administered using commercially available nebulizers. Formulation in a fatty acid source may be used to enhance biocompatibility.

For rectal administration, the active ingredient may be formulated into suppositories using bases which are solid at room temperature and melt or dissolve at body temperature. Commonly used bases include cocoa butter, glycerinated gelatin, hydrogenated vegetable oil, polyethylene glycols of various molecular weights, and fatty esters of polyethylene stearate.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, and the particular compound employed, the location of the unwanted proliferating cells, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administrated may need to be optimized for each individual. The pharmaceutical compositions may contain active ingredient in the range of about 0.1 to 2000 mg in some embodiments, in the range of about 0.5 to 500 mg in other embodiments, and between about 1 and 200 mg in still other embodiments. In some embodiments, a daily dose of about 0.01 to 100 mg/kg body weight is appropriate. In other embodiments, a daily dose of between about 0.1 and about 50 mg/kg body weight, may be appropriate. The daily dose can be administered in single or multiple doses per day.

Synthesis of 1-N-sulfonamides. Indol-3-carboxaldehyde (1.0 mmol) was treated with NaH (1.0 mmol) in THF at 0° C. for 30 min., sulfonyl chloride (1.0 mmol) was added slowly. The reaction mixture was warmed up and refluxed for 2 to 6 hrs, then concentrated, diluted with ethyl acetate, washed with water and brine, dried over Na2SO4. Solvent was removed and the residue was purified with column chromatography gave pure product.

Synthesis of 1-N-carboxamides. Indol-3-carboxaldehyde (1.0 mmol) was treated with NaOH (1.0 mmol) in THF at 0° C. for 30 min., carbonyl chloride (1.0 mmol) was added slowly. The reaction mixture was warmed up to room temperature and stirred for 12 to 16 hrs, then concentrated, diluted with ethyl acetate, washed with water and brine, dried over Na2SO4. Solvent was removed and the residue was purified with column chromatography gave pure product.

Reduction of 1-N-substituted indole-3-carboxaldehyde with NaBH4. To the solution of sulfonamide (1.0 mmol) in methanol, NaBH4 (1.0 mmol) in methanol was added slowly at 0° C. After addition complete, the reaction was warmed up to room temperature, stirred for 1 hr (checked with TLC), 10 ml of 1N HCl was added after reaction completed. Concentrated, diluted with water (20 ml) and extracted with ethyl acetate (3×20 ml). The combined organic layers was washed with water, 10% NaHCO3, and brine, dried with MgSO4, filtered and concentrated. The residue was purified with column chromatography gave pure reduction product.

Synthesis of 1-substituted indole-3-carboxaldehyde oxime. To a stirred solution of corresponding aldehyde (1.0 mmol) in ethanol (5 ml) was added a solution of hydroxylammonium chloride (104 mg, 1.5 mmol) and sodium carbonate (77 mg, 0.72 mmol) in water (0.5 ml), and the mixture was stirred with heating for 5 to 30 min at 60 to 90° C. After evaporation of ethanol and addition of water (10 ml), the oxime precipitated as solid, collected with filtration, dried and crystallized from ethyl/water.

Synthesis of 1-substituted indole-3-ylmethyl amine salt. To a solution of NiCl2.6H2O (238 mg, 1.0 mmol) in methanol (15 ml) was added corresponding oxime (1.0 mmol) and NaBH4 (248 mg, 6.5 mmol) was added in one portion with stirring. After 5 to 10 min the reaction mixture was filtered and the filtrate was concentrated. The residue (about 5 ml) was diluted with 50 ml of water and 5 ml of 28-30% NH4OH, extracted with ethyl acetate (3×20 ml), the combined organic layers was dried with Na2SO4, filtered, treated with HCl ether solution and concentrated to give crude amines solid. Crystallization from ethanol afforded pure amine salt.

Provided herein are antitumor agents with improved chemical stability and apoptosis-inducing potency as compared to indole-3-carbinol. In one exemplary embodiment, OSU-A9, is an acid-stable analogue with two-orders-of-magnitude higher apoptosis-inducing potency than the parental indole-3-carbinol. Moreover, OSU-A9 retained the pleiotropic effects of indole-3-carbinol on multiple signaling targets associated with growth arrest and apoptosis. Equally important, despite this broad spectrum of pharmacological activities, normal prostate epithelial cells were less sensitive to the antiproliferative effect of OSU-A9 relative to prostate cancer cell lines.

Materials and Methods

Reagents. 1H-Indole-3-carbaldehyde (Sigma-Aldrich, St. Louis, Mo.) was used as the starting material to synthesize 1H-indole-3-carbinol and series I-III derivatives (Table I). The identity and purity ($\geq$99%) of these synthetic derivatives were verified by proton nuclear magnetic resonance, high-resolution mass spectrometry, and elemental analysis. For in vitro experiments, these agents at various concentrations were dissolved in DMSO, and were added to cells in medium with a final DMSO concentration of 0.1%. Rabbit polyclonal antibodies against various biomarkers were obtained from the following sources: p-$^{473}$Ser Akt, p-Bad, Bad, p-ERKs, p-JNK, JNK, p-p38, p38, cyclin D1 and NF-kB, Cell Signaling Technologies (Beverly, Mass.); Akt, ERKs, p27, p21, Bax, Bcl-2, Bcl-xL and AR, Santa Cruz Biotechnology (Santa Cruz, Calif.); survivin, R&D Systems (Minneapolis, Minn.); β-actin, Sigma-Aldrich (St. Louis, Mo.). Mouse monoclonal anti-poly(ADP-ribose) polymerase (PARP) antibody was purchased from Pharmingen (San Diego, Calif.). The enhanced chemiluminescence (ECL) system for detection of immunoblotted proteins was from GE Healthcare Bioscience (Piscataway, N.J.). Other chemicals and biochemistry reagents were obtained from Sigma-Aldrich unless otherwise mentioned.

Cell Culture. LNCaP androgen-responsive (p53$^{+/+}$) and PC-3 androgen-nonresponsive (p53$^{-/-}$) human prostate cancer cells were purchased from the American Type Tissue Collection (Manassas, Va.) and cultured in RPMI 1640 medium (Gibco, Grand Island, N.Y.) supplemented with 10% fetal bovine serum (FBS; Gibco).—Normal human prostate epithelial cells (PrEC) were obtained from Cambrex Bioscience-Walkersville (Walkersville, Md.), and maintained in the vendor's recommended defined prostate epithelial growth medium. All cell types were cultured at 37° C. in a humidified incubator containing 5% $CO_2$.

Cell viability analysis. The effect of test agents on cell viability was assessed by using the MTT [3-(4,5-dimethylthiazol-2-yl)-2,5-diphenyl-2H-tetrazolium bromide] assay in six to twelve replicates. Cancer cells and PrECs were grown in 5% FBS-supplemented RPMI 1640 medium or 5% FBS-supplemented prostate epithelial growth medium, respectively, in 96-well, flat-bottomed plates for 24 h, and then exposed to various concentrations of test agents in the same medium for the indicated time intervals. Controls received DMSO vehicle at a concentration equal to that in drug-treated cells. At the end of the treatment, the medium was removed, replaced by 200 μL of 0.5 mg/mL of MTT in the same medium, and cells were incubated in the $CO_2$ incubator at 37° C. for 2 h. Supernatants were removed from the wells, and the reduced MTT dye was solubilized in 200 μL/well DMSO. Absorbance at 570 nm was determined on a plate reader.

Cell Proliferation. PC-3 and LNCaP cells were seeded into six-well plates at approximately 200,000 cells/well in 5% FBS-containing RPMI 1640 medium. Following a 24 h attachment period, cells were treated in triplicate with the indicated concentrations of test agent or DMSO vehicle in 5% FBS-containing RPMI-1640 medium. At different time intervals, cells were harvested by trypsinization, and numerated using a Coulter counter (Model Z1 D/T, Beckman Coulter, Fullerton, Calif.).

Apoptosis analysis. Drug-induced apoptotic cell death was assessed by Western blot analysis of caspase-3 activation and poly-(ADP-ribose)polymerase (PARP) cleavage. Drug-treated cells were collected after 48 h of treatment, washed with ice-cold PBS, and resuspended in lysis buffer containing 20 mM Tris-HCl, pH 8, 137 mM NaCl, 1 mM $CaCl_2$, 10% glycerol, 1% Nonidet P-40, 0.5% deoxycholate, 0.1% SDS, 100 μM 4-(2-aminoethyl)benzenesulfonyl fluoride, leupeptin at 10 μg/mL, and aprotinin at 10 μg/mL. Soluble cell lysates were collected after centrifugation at 10,000 g for 5 min. Equivalent amounts of proteins (60-100 μg) from each lysate were resolved in 8% SDS-polyacrylamide gels. Proteins were transferred to nitrocellulose membranes, and analyzed by immunoblotting with antibodies against caspase-3 or PARP as described below.

Immunoblotting. Biomarkers of apoptosis and signaling components associated with cell survival and growth arrest were assessed by Western immunoblotting as follows. Treated cells were washed in PBS, resuspended in SDS sample buffer, sonicated for 5 sec, and then boiled for 5 min. After brief centrifugation, equivalent amounts of proteins from the soluble fractions of cell lysates were resolved in 10% SDS-polyacrylamide gels on a Minigel apparatus, and transferred to a nitrocellulose membrane using a semi-dry transfer cell. The transblotted membrane was washed three times with TBS containing 0.05% Tween 20 (TBST). After blocking with TBST containing 5% nonfat milk for 60 min, the membrane was incubated with an appropriate primary antibody at 1:500 dilution (with the exception of anti-b-actin antibody, 1:2,000) in TBST-5% low fat milk at 4° C. for 12 h, and was then washed three times with TBST. The membrane was probed with goat anti-rabbit or anti-mouse IgG-horseradish peroxidase conjugates (1:2,500) for 90 min at room temperature, and washed three times with TBST. The immunoblots were visualized by enhanced chemiluminescence.

Molecular modeling. Molecular structures of A7, OSU-A9, and A12, were subjected to energy minimization using the Merck Molecular Force Field program available as part of the Macromodel 7.0 software package (Schrodinger, Portland, Oreg.; http://www.schrodinger.com). The minimum conformations were then fully optimized at a density functional theory level of B3LYP/6-31G* basis set using Gaussian 03 (Gaussian, Inc., Pittsburgh, Pa.). All of the fully optimized structures were confirmed by normal mode analysis; no negative frequencies were found. Computations for electron density and electrostatic potential were then carried out for each of the fully optimized structures with a grid of 216,000 points using Gaussian 03. Molecular electrostatic potential maps for each compound were generated with the electrostatic potential mapped onto the electron density. The electron density isosurface value was 0.002 (electron/Å) with a range of −0.03 to 0.03 for the electrostatic potential. All molecular modeling calculations and manipulations were performed on Silicon Graphics O2 (Silicon Graphics Inc.; Mountain View, Calif.).

Nuclear magnetic resonance (NMR) analysis of acid stability. Indole-3-carbinol and OSU-A9, 20 mg each, were dissolved in 1 ml of $CD_3OD$. To each solution was added 100 μl of deuterium-labeled HCl, and NMR spectra were recorded in a 300 MHz NMR spectrometer at room temperature at different time intervals.

Luciferase assay for PPARg activation. The PPRE-x3-TK-Luc reporter vector contains three copies of the PPAR-response element (PPRE) upstream of the thymidine kinase (tk) promoter-luciferase fusion gene and was kindly provided by Dr. Bruce Spiegelman (Harvard University, Cambridge, Mass.). PC-3 cells were cultured in a 100 mm plate in phenol red-free RPMI 1640 medium containing 10% FBS until the achieved 50-70% confluency, after which they were transfected with 6 μg of the plasmid using Fugene 6 (Roche, Indianapolis, Ind.) in RPMI 1640 medium. For each transfection, herpes simplex virus-thymidine kinase (HSV-TK) promoter-driven *Renilla* luciferase (phRL-TK) was used as an internal control for normalization. Following transfections, cells were treated as indicated, in RPMI 1640 medium containing 10% charcoal-stripped FBS. Cells were then collected into Passive Lysis Buffer (Promega), and luciferase activities in the cell lysates were determined by luminometry. All transfection experiments were carried out in triplicate plates and repeated separately at least three times.

In vivo studies. Intact male NCr athymic nude mice (5-7 weeks of age) were obtained from the National Cancer Institute (Frederick, Md.). The mice were group housed under conditions of constant photoperiod (12 hours light: 12 hours dark) with ad libitum access to sterilized food and water. All experimental procedures utilizing these mice were performed in accordance with protocols approved by the Institutional Laboratory Animal Care and Use Committee of The Ohio State University. Each mouse was inoculated subcutaneously in the right flank with $5 \times 10^5$ PC-3 cells in a total volume of 0.1 mL serum-free medium containing 50% Matrigel (BD Biosciences, Bedford, Mass.) under isoflurane anesthesia. As tumors became established (mean starting tumor volume, $109 \pm 10$ mm$^3$), mice were randomized to three groups (n=7) that received the following treatments: (a) OSU-A9 at 10 mg/kg body weight q.d., (b) OSU-A9 at 25 mg/kg q.d., (c) DMSO vehicle. Mice received treatments by intraperitoneal injection (50 μL/mouse) for the duration of the study. Tumors were measured weekly using calipers and their volumes calculated using a standard formula: width2×length×0.52. Body weights were measured weekly. At terminal sacrifice, a complete necropsy was performed on all mice and PC-3 tumors were harvested. A portion of each tumor was snap-frozen in liquid nitrogen and stored at $-80°$ C. until needed for western blot analysis of relevant biomarkers, and the remainder was fixed in 10% formalin. All other tissues were fixed overnight in 10% formalin then transferred to 70% ethanol. Four μm-thick, paraffin-embedded tissue sections were stained with hematoxylin and eosin by standard procedures. A core list of tissues from three mice per group were evaluated microscopically animal by animal by a veterinary pathologist in accordance with Society of Toxicologic Pathology-proposed guidelines for repeat-dose toxicity studies, with the exception of spinal cord and thymus. Blood from each mouse was submitted to The Ohio State University Veterinary Clinical Laboratory Services for evaluation of serum chemistry and hematological parameters.

Statistical analysis. Differences in relative PPARγ activation in vitro and among group means of tumor volume in vivo were analyzed for statistical significance using one-way ANOVA followed by the Neuman-Keuls test for multiple comparisons. Differences were considered significant at $P<0.05$. Statistical analyses were performed using SPSS for Windows (SPSS, Inc., Chicago, Ill.).

We synthesized three series of N-substituted analogues: (1-aryloyl-1H-indol-3-yl)-methanols (I), (1-arylsulfonyl-1H-indol-3-yl)-carbaldehydes (II), and (1-arylsulfonyl-1H-indol-3-yl)-methanols (III), shown in the table below.

TABLE I

Structures and Antiproliferative Activities of Indole-3-Carbinol Derivatives

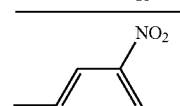

| R | | I | | | II | | | III | | |
|---|---|---|---|---|---|---|---|---|---|---|
| | | | IC$_{50}$ (μM) | | | IC$_{50}$ (μM) | | | IC$_{50}$ (μM) | |
| | No. | PC-3 | LNCaP | No. | PC-3 | LNCaP | No. | PC-3 | LNCaP | |
| 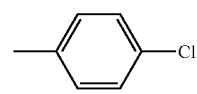 NO$_2$ | A1 | >50 | >50 | A2 | 29 | >50 | A3 | 24 | 32 | |
| Cl | A4 | >50 | >50 | A5 | >50 | >50 | A6 | 42 | >50 | |

TABLE I-continued

Structures and Antiproliferative Activities of Indole-3-Carbinol Derivatives

| R | | | | | | | | |
|---|---|---|---|---|---|---|---|---|
| 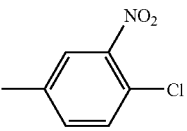 2-NO2, 4-Cl phenyl | A7 | >50 | >50 | A8 | 8 | 15 | A9 | 2 | 3.8 |
| 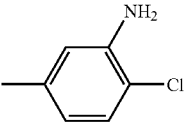 2-NH2, 4-Cl phenyl | A10 | >50 | >50 | A11 | >50 | >50 | A12 | >50 | >50 |
| 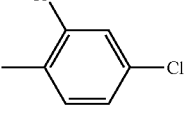 2,4-diCl phenyl | A13 | >50 | >50 | A14 | 24 | 40 | A15 | 40 | >50 |
| 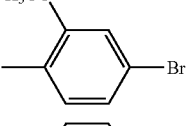 2-OMe, 4-Br phenyl | A16 | >50 | >50 | A17 | 26 | 44 | A18 | >50 | >50 |
|  4-Br phenyl | A19 | >50 | >50 | A20 | 38 | 20 | A21 | 40 | >50 |
| 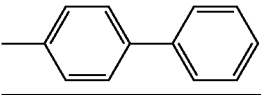 biphenyl | A22 | >50 | >50 | A23 | 14 | 16 | A24 | 36 | >50 |

Figure 2A:
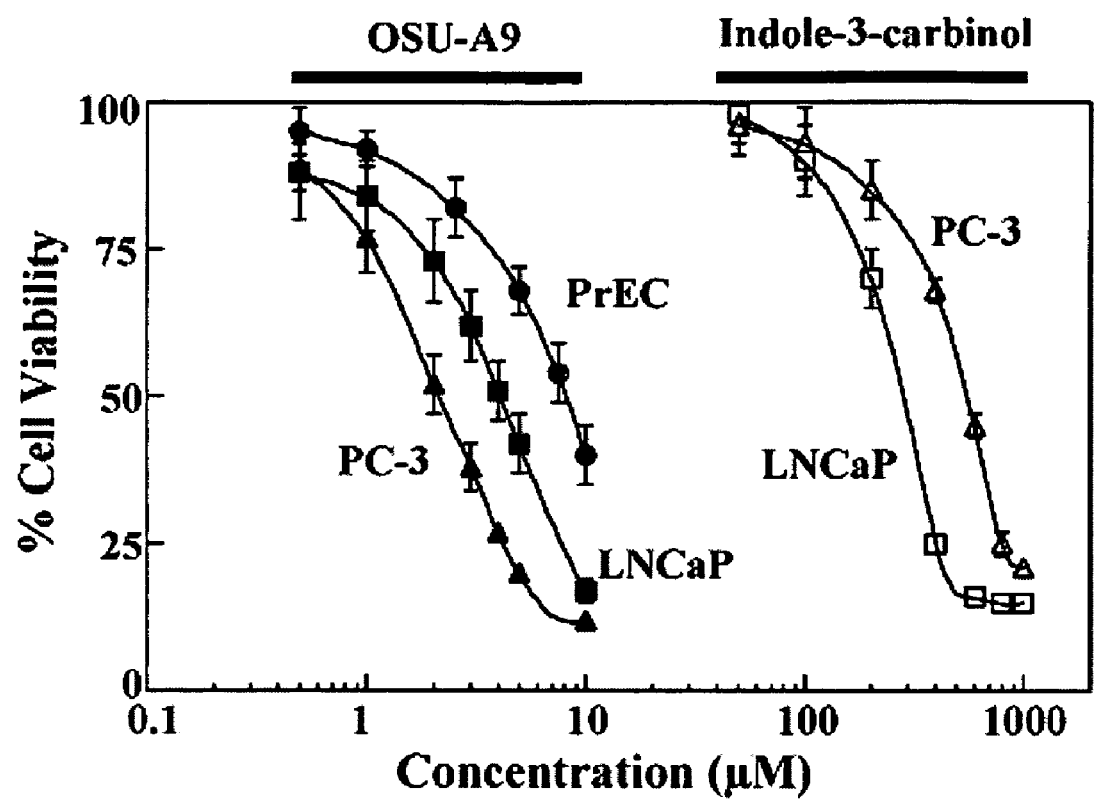
FIGS. 2 a-b show the antiproliferative effects of OSU-A9 and indole-3-carbinol in two prostate cancer cell lines and PrECs. A, effect of OSU-A9 on the viability of PrECs, and PC-3 and LNCaP prostate cancer cells versus that of indole-3-carbinol in PC-3 and LNCaP cells. Cells were treated with OSU-A9 or indole-3-carbinol at the indicated concentrations in 5% FBS-supplemented RPMI 1640 medium in 96-well plates for 48 h, and cell viability was assessed by MTT assays. Points, mean; bars, SD (n=6). B, dose-dependent antiproliferative effect of indole-3-carbinol (a, DMSO vehicle; b, 100 μM; c, 200 μM; d, 300 μM; e, 400 μM; f, 500 μM) versus OSU-A9 (a, DMSO vehicle; b, 0.5 μM; c, 1 μM; d, 2.5 μM; f, 5 μM) in PC-3 and LNCaP cells. Cells were seeded onto six-well plates (200,000 cells/well) and exposed to the test agent at the indicated concentrations in 5% FBS-supplemented RPMI 1640 medium. At different time intervals, cells were harvested, and counted using a Coulter counter. Values were obtained from triplicates.

These agents (A1-A24) were evaluated for their ability to reduce cell viability of PC-3 (p53$^{-/-}$) androgen-nonresponsive and LNCaP (p53$^{+/+}$) androgen-responsive prostate cancer cells after 24-h exposure by MTT assay. While the IC$_{50}$ values of all carboxamide derivatives (series I) were greater than 50 μM, some of the derivatives in the II and III series showed improved antitumor activities vis-à-vis indole-3-carbinol. Especially noteworthy is the compound A9, which exhibited IC$_{50}$ values of 2 μM and 3.8 μM for PC-3 and LNCaP cells, respectively. This antitumor potency was two-orders-of-magnitude higher than that of indole-3-carbinol (respective IC$_{50}$, 512 μM and 267 μM) (FIG. 2A). Moreover, assessment of effects on nonmalignant cells revealed that PrECs exhibited a 2.2-4.5-fold lower sensitivity to OSU-A9 (IC$_{50}$, 9 μM) than the prostate cancer cells (FIG. 2A).

Figure 2B:
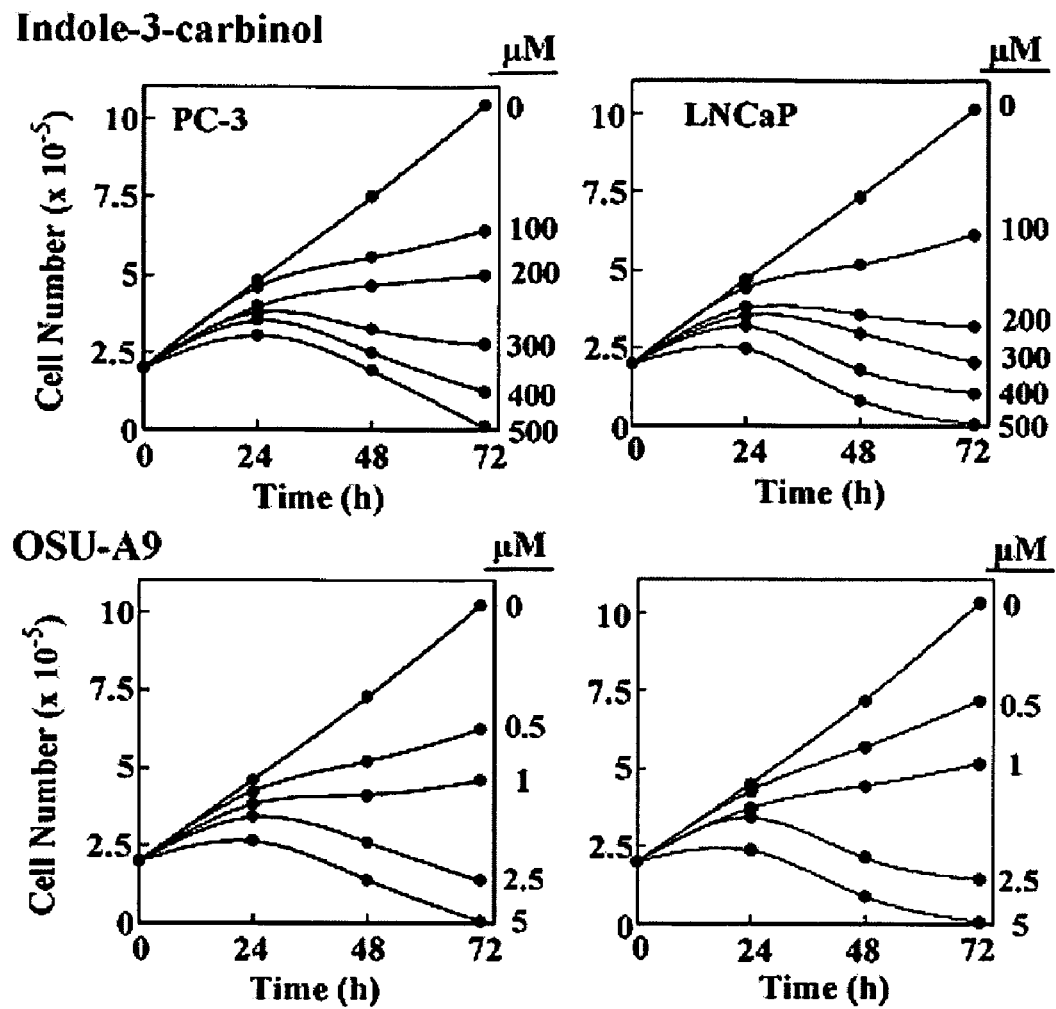

The in vitro efficacy of OSU-A9 vis-à-vis indole-3-carbinol in inhibiting the proliferation of PC-3 and LNCaP cells was also examined by direct counting of drug-treated cells (FIG. 2B). OSU-A9, at 2.5 μM and above, completely suppressed cell proliferation and cause a net decrease in cell numbers in both cell lines, indicative of cytocidal activity. In line with the cell viability data, a concentration of at least 300 μM was required for indole-3-carbinol to attain the same level of efficacy.

Molecular modeling analysis. The structure-activity analysis revealed that changes in OSU-A9's structure, such as substitution of the sulfonyl (—SO$_2$—) linker with a carbonyl (—CO—) function (i.e., A7) or replacement of the nitro (—NO$_2$) substituent with an amino (—NH$_2$) moiety (i.e., A12), resulted in a loss of antitumor activity. To shed light onto the structural basis underlying this subtle structure-activity relationship, we analyzed the configuration and surface electrostatic potential of OSU-A9 versus those of A7 and A12 via modeling analysis.

OSU-A9 and A7 assumed vastly different configurations resulting from the structural differences between the tetrahedron-like sulfonyl (—SO$_2$—) and the triagonal-planar carbonyl (—CO—) linkers. The electropositive nature of the nitro-substituent on the appended phenyl ring increased the ability of OSU-A9 to induce apoptosis. Replacement of the electron-withdrawing nitro-group with an electron-donating amino function, as in A12, changed the regional surface potential, resulting in the diminishment of apoptosis-inducing activity.

OSU-A9 resists acid-catalyzed dimerization. We used a nuclear magnetic resonance (NMR) technique to analyze the chemical stability of OSU-A9 versus indole-3-carbinol in 0.1 N HCl by monitoring changes in the proton signal associated with C$\underline{H}_2$OH. Individual compounds (20 mg) were dissolved in 1 ml of deuterium-labeled methanol (CD$_3$OD). The NMR spectra revealed signals for the methylene protons (indicated by *) at 4.73 ppm and 4.74 ppm for indole-3-carbinol and OSU-A9, respectively (upper spectra, left and right panels). Addition of 100 μl of 0.1 N deuterium-labeled HCl to indole-3-carbinol resulted in an immediate shift of the C$\underline{H}_2$ signal from 4.73 ppm to 4.66 ppm (t=5 min), indicating the chemical transformation of indole-3-carbinol to an acid reaction mixture consisting of DIM and other oligomeric products. On the other hand, no appreciable change in the spectrum was noted after exposure of OSU-A9 to HCl for up to 8 h, indicating its significantly greater chemical stability.

OSU-A9 facilitates apoptosis by targeting multiple signaling pathways identical to that of indole-3-carbinol. Several lines of evidence suggest that the antiproliferative effect of OSU-A9 was, at least in part, attributable to apoptosis, reminiscent of that of indole-3-carbinol. Light microscopic examination revealed that 5 µM OSU-A9 and 500 µM indole-3-carbinol caused pronounced morphological changes in PC-3 cells after treatment for 24 h and 48 h, respectively. Drug-treated cells became shrunken, rounded, and detached from the dish. Western blot analysis showed a dose-dependent effect of both agents on caspase-3 activation and PARP cleavage after treatment for 48 hours. The effects of indole-3-carbinol and OSU-A9 on these two apoptosis-related biomarkers were qualitatively similar, albeit with a 100-fold difference in potency.

Figure 3:
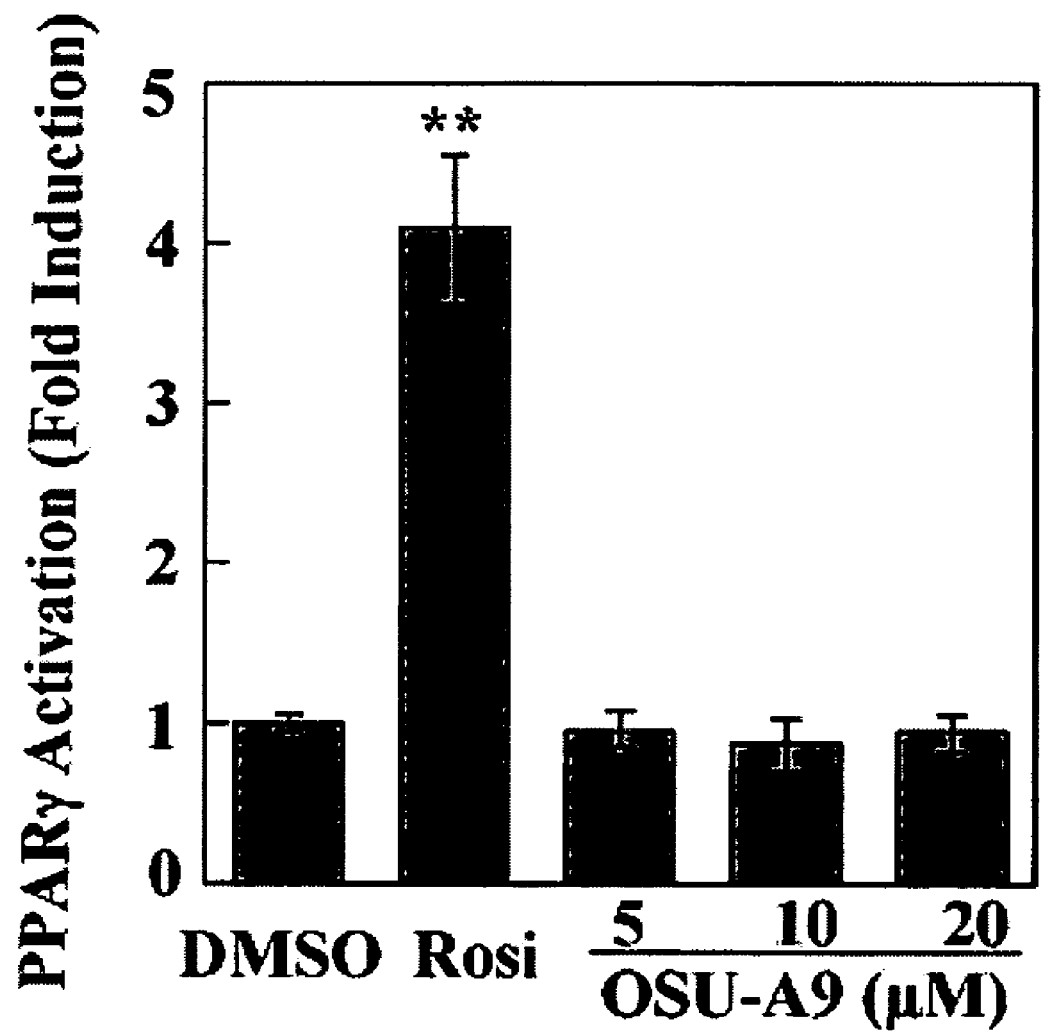
FIG. 3 shows pharmacological evidence that the apoptotic effect of OSU-A9 in PC-3 cells is independent of PPARγ activation. PC-3 cells were transfected with PPRE-X3-TK-Luc and treated with 10 μM rosiglitazone (Rosi) or the indicated concentrations of OSU-A9 for 24 h, and luciferase activity was determined as described in the Materials and Methods. Columns, mean; bars, SD (n=3). **, P<0.01.

From a translational perspective, the mechanism by which OSU-A9 mediated antiproliferative effects warranted investigation. The finding that many indole derivatives including DIMs exhibited PPARγ agonist activity raised the possibility that PPARγ activation might contribute to the apoptosis-inducing effect of OSU-A9. Accordingly, we used a PPRE-luciferase reporter assay to assess the ability of OSU-A9 to transactivate PPARγ in PC-3 cells. However, even at 20 µM, OSU-A9 lacked appreciable activity in PPARγ transactivation (FIG. 3).

Figure 4:
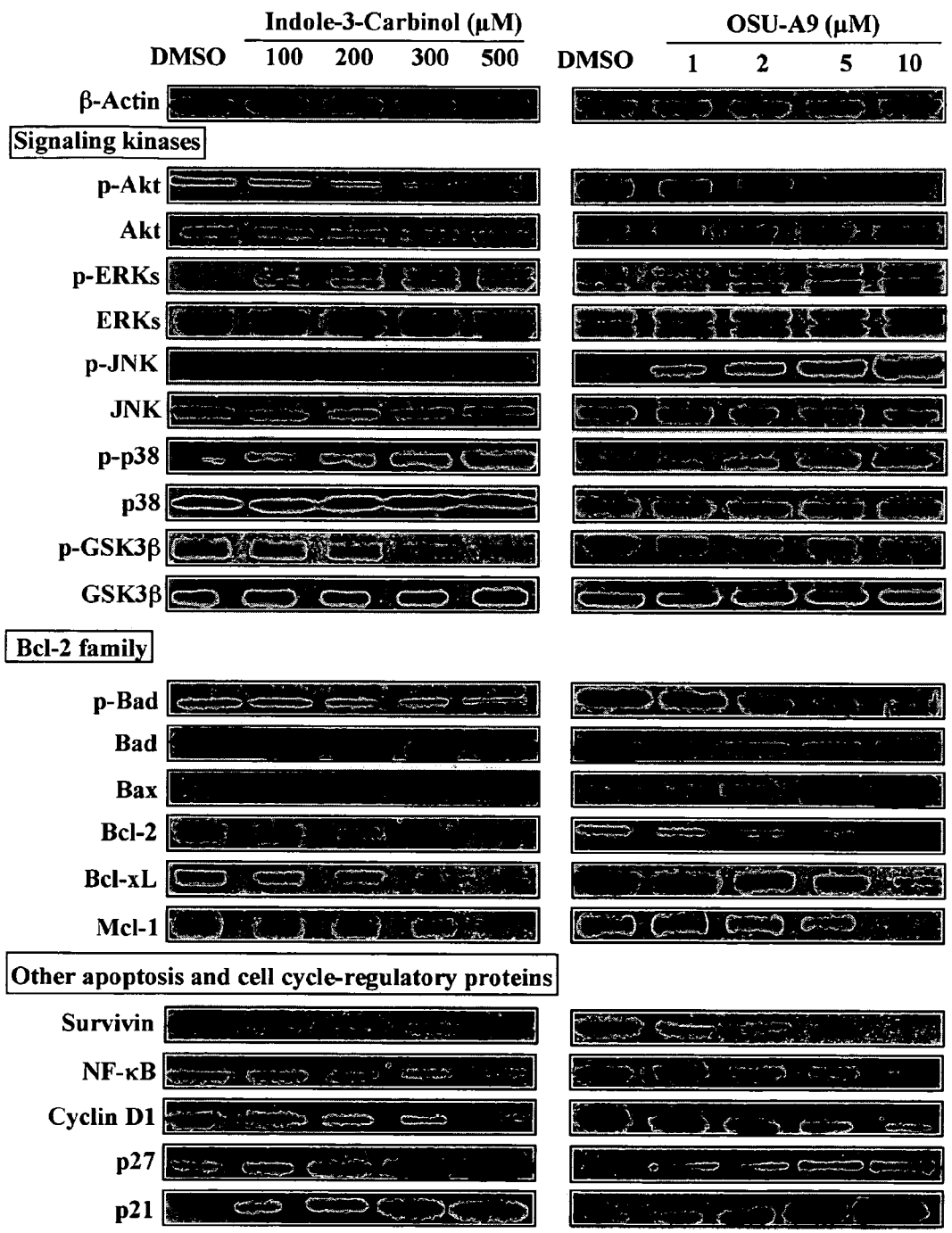
FIG. 4 shows dose-dependent effects of OSU-A9 versus indole-3-carbinol on the phosphorylation of Akt, ERKs, JNK, p38, GSK3β, and Bad, and the expression levels of Bax, Bcl-2, Bcl-xL, Mcl-1, survivin, NF-kB, cyclin D1, p27, and p21 in PC-3 cells. Cells were treated with the indicated concentrations of indole-3-carbinol or OSU-A9 in 5% FBS-supplemented RPMI 1640 medium for 48 h, and cell lysates were immunoblotted as described in Materials and Methods. These data suggest that OSU-A9 retains the pleiotropic effects of indole-3-carbinol in regards to the activating apoptosis machinery by targeting multiple signaling pathways.

Indole-3-carbinol has been reported to target an array of signaling pathways to induce apoptosis and cell cycle arrest in cancer cells. Consequently, we examined the dose-dependent effect of OSU-A9 vis-à-vis indole-3-carbinol in PC-3 cells on the phosphorylation and/or expression status of a series of molecular targets reported for indole-3-carbinol in the literature. These targets comprised three categories of biomarkers: a) phosphorylation of signaling kinases: Akt and its downstream effector GSK3β, ERKs, JNKs, and p38; b) phosphorylation/expression of Bcl-2 family members: Bad, Bax, Bcl-2, Bcl-xL, and Mcl-1; c) expression of other apoptosis and cell-cycle regulatory proteins: survivin, NF-kB/RelA, cyclin D1, p27, and p21 (FIG. 4).

Despite a 100-fold difference in antitumor potency, the pharmacological profiles of OSU-A9 and indole-3-carbinol in interfering with these target proteins were virtually identical. As shown, both agents facilitated dose-dependent dephosphorylation of Akt and its substrates GSK3b and Bad, accompanied by increased phosphorylation of ERKs, JNK, and p38. Moreover, the dose-dependent effects of OSU-A9 on suppressing the expression of Bcl-2, Bcl-xL, Mcl-1, survivin, NF-kB, and cyclin D1, and on up-regulating the expression of Bax, p27, and p21 paralleled those of indole-3-carbinol. However, in contrast to an earlier report that indole-3-carbinol suppressed the expression of androgen receptor (AR) in LNCaP cells, the present data indicate that neither agents had an appreciable effect on AR expression even at the respective highest doses examined (data not shown).

Together, these data suggest that OSU-A9 retains the pleiotropic effects of indole-3-carbinol in regards to the activating apoptosis machinery by targeting multiple signaling pathways. Pursuant to these findings, the in vivo antitumor potential of OSU-A9 was further assessed in a PC-3 xenograft animal model.

OSU-A9 suppresses PC-3 tumor xenograft growth in vivo. The maximum tolerated dose of OSU-A9 in athymic nude mice was determined by intraperitoneal injection at 5, 10, 25, and 50 mg/kg/day (n=3) continuously for 14 days. No apparent weight loss was noted at doses up to 25 mg/kg.

Figure 5:
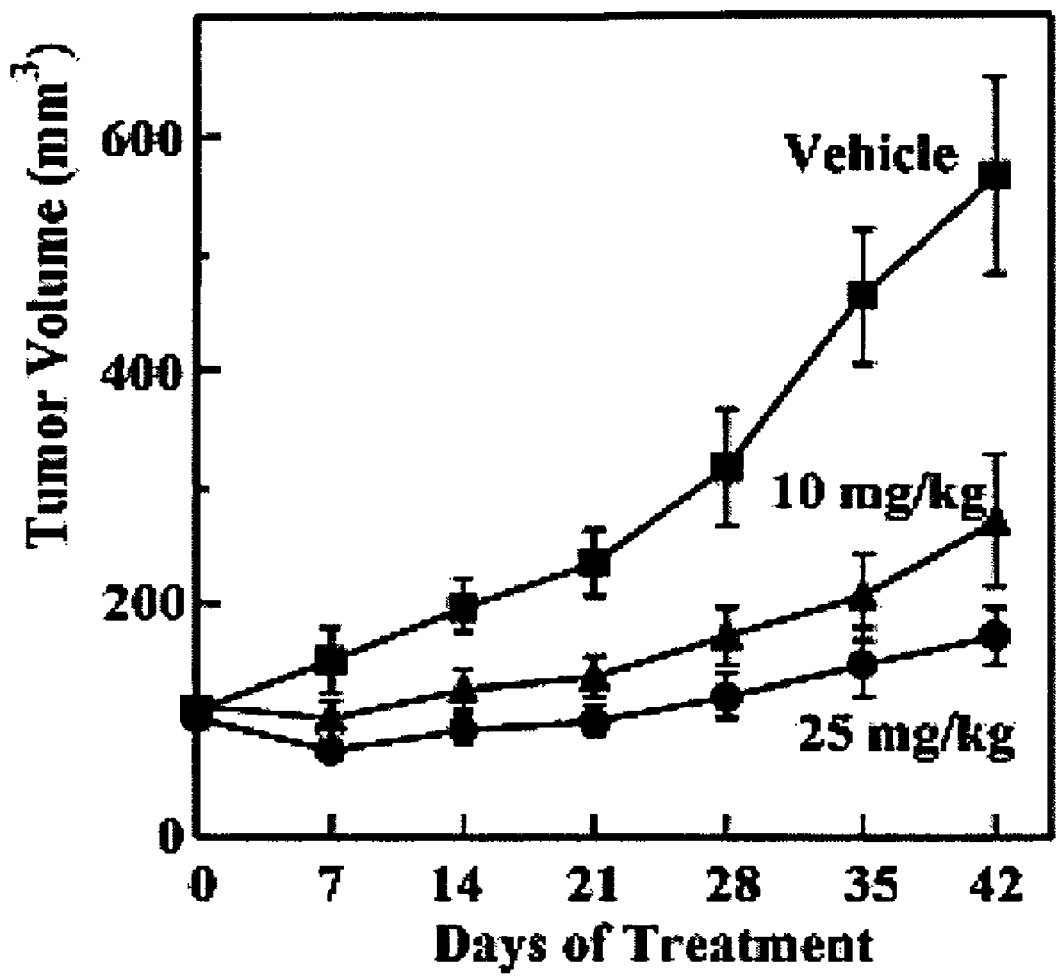
FIG. 5 shows the effects of OSU-A9 at 10 mg/kg or 25 mg/kg per day, administered intraperitoneally, on the growth of established PC-3 tumors in nude mice and the expression of intratumoral biomarkers of drug activity. Points, mean tumor volume; bars, SEM (n=7). Subcutaneous PC-3 tumor xenografts were established and treatments administered as described in the Materials and Methods. OSU-A9 significantly inhibited PC-3 tumor growth by 66% and 85%, respectively, relative to vehicle-treated controls (P<0.01). Importantly, mice appeared to tolerate treatment with OSU-A9 without overt signs of toxicity, without significant loss of body weight compared to vehicle-treated controls, and with normal hematological and serum chemistry findings. The sole lesions observed at necropsy in all OSU-A9-treated mice were mild to moderate amounts of fibrous adhesions that were limited to the peritoneal surfaces of tissues including the colon, seminal vesicles, and body wall, and did not appear to compromise function. Microscopically, there were no treatment-associated lesions in the array of tissues examined in the OSU-A9-treated mice, with the exception of the affected peritoneum, which was variably expanded by mixtures of granulation and fibrous tissue and activated macrophages. No lesions were observed in the vehicle-treated controls.

To examine the in vivo antitumor efficacy of OSU-A9, athymic nude mice bearing established subcutaneous PC-3 tumor xenografts (mean tumor volume, 109±10 mm$^3$) were treated intraperitoneally for 42 days with OSU-A9 at 10 mg/kg or 25 mg/kg daily, or with vehicle. As shown in FIG. 5, treatment of mice with 10 and 25 mg/kg of OSU-A9 significantly inhibited PC-3 tumor growth by 66% and 85%, respectively, relative to vehicle-treated controls (P<0.01). Importantly, mice appeared to tolerate treatment with OSU-A9 without overt signs of toxicity, without significant loss of body weight compared to vehicle-treated controls, and with normal hematological and serum chemistry findings. The sole lesions observed at necropsy in all OSU-A9-treated mice were mild to moderate amounts of fibrous adhesions that were limited to the peritoneal surfaces of tissues including the colon, seminal vesicles, and body wall, and did not appear to compromise function. Microscopically, no significant lesions were present in the tissues examined in the OSU-A9-treated mice, with the exception of the affected peritoneum, which was variably expanded by mixtures of granulation and fibrous tissue and activated macrophages. No lesions were observed in the vehicle-treated controls.

To correlate this in vivo tumor suppressive response to mechanisms identified in vitro, the effects of OSU-A9 on six representative intratumoral biomarkers of drug activity were evaluated by immunoblotting of PC-3 tumor homogenates collected after 42 days of treatment. These biomarkers included the phosphorylation status of Akt and p38, and expression levels of Bcl-xL, NF-kB/RelA, cyclin D1, and p27. The effects of OSU-A9 on these biomarkers were qualitatively similar to those observed in vitro, and reflect the dose-dependent tumor suppression in vivo. Treatment with OSU-A9 intraperitoneally at 10 and 25 mg/kg per day induced marked reductions in intratumoral levels of phospho-Akt (83±8% and 94±1% reductions, respectively, compared to vehicle-treated controls), Bcl-xL (34±8% and 86±4%, respectively), RelA (60±7% and 77±7%, respectively), and cyclin D1 (70±3% and 88±3%, respectively), accompanied by increases in intratumoral levels of phospho-p38 (9.0±3.5-fold and 10.1±2.4-fold, respectively) and p27 (1.8±0.3-fold and 2.7±1.4-fold, respectively).

During the course of tumor progression, cancer cells constitutively up-regulate cell proliferation- and cell survival-regulatory signaling mechanisms, thereby overcoming genomic instability and/or acquiring a drug-resistant phenotype. From a clinical perspective, it is desirable to concomitantly target these molecular abnormalities by using a combination therapy or an agent with pleiotropic effects to optimize therapeutic outcomes. This rationale constitutes the molecular basis for structurally optimizing indole-3-carbinol to develop potent antitumor agents. This effort has culminated in the generation of OSU-A9, which provides considerable therapeutic advantages over indole-3-carbinol with respect to chemical stability and anti-tumor potency.

The introduction of a (3-chloro-2-nitrobenzene)sulfonyl substituent onto the indole nucleus endowed OSU-A9 with resistance to acid-catalyzed dehydration, and, equally important, a 100-fold higher apoptosis-inducing potency. Relative to indole-3-carbinol, OSU-A9 displayed a strikingly similarity in the effects on modulating the phosphorylation or expression of a multitude of molecular targets, including Akt and its downstream effectors GSK3β and Bad, the MAP kinases ERKs, p38, and JNK, the Bcl-2 family members Bax, Bcl-2, Bcl-xL, and Mcl-1, the inhibitor of apoptosis protein (IAP) survivin, NF-kB, cyclin D1, and the CDK inhibitors p21 and p27. These signaling proteins regulate cell cycle and apoptosis at multiple levels, including transcriptional activation of gene expression, cell cycle checkpoint control, intracellular kinase signaling, mitochondrial integrity, and caspase activation, all of which are clinically relevant to the tumorigenesis and progression of prostate cancer. This broad range of antitumor activities underscores the in vitro and in vivo efficacy of OSU-A9 and related compounds in prostate cancer cells. It is especially noteworthy that, despite this complicated mode of drug action, normal prostate epithelial cells were less susceptible to the antiproliferative effect of OSU-A9, reflecting the in vivo tolerance of this drug in tumor-bearing nude mice.

Assessment of the in vivo efficacy in tumor-bearing nude mice indicate that daily intraperitoneal injection of OSU-A9 at 10 and 25 mg/kg per day for 42 days resulted in a 65% and 85%, respectively, suppression of established PC-3 xenograft tumor growth. Western blot analysis of the tumor lysates revealed that the extent of changes in the six representative biomarkers paralleled the dose-dependent tumor-suppressive activity of OSU-A9. The concerted action on these molecular targets underscores the therapeutic potential of OSU-A9 to be developed into a potent antitumor agent not only as a single agent, but also potentially in combination with other chemotherapeutic drugs. Previously, indole-3-carbinol was shown to sensitize prostate and breast cancer cells to cisplatin and tamoxifen, respectively OSU-A9 was well-tolerated by tumor-bearing mice following 6 weeks of repeat dosing. The absence of gross and microscopic lesions in major organs together with normal clinical and hematologic findings indicated that the intra-abdominal fibrous adhesions observed in the OSU-A9-treated animals were likely non-specific reactions associated with chronic irritation induced by intraperitoneal injection of the drug. While concerns regarding potential toxicities arising from the use of drugs with pleiotropic actions warrant consideration, our findings suggest that, at least in the case of OSU-A9, such adverse effects are not an obligatory consequence.

Through this study, OSU-A9, was shown to be a potent antitumor agent that modulates multiple aspects of cancer cell cycle regulation and survival, including intracellular kinase signaling, cell cycle checkpoint control, mitochondrial integrity, and caspase activation. This broad spectrum of antitumor activities in conjunction with low toxicity underlies the translational potential of OSU-A9, and suggests its viability as part of a therapeutic strategy for prostate cancer.

The examples provided herein are for illustrative purpose only and does not limit the scope of the invention as defined in the claims.

The invention claimed is:

1. A compound of formula I:

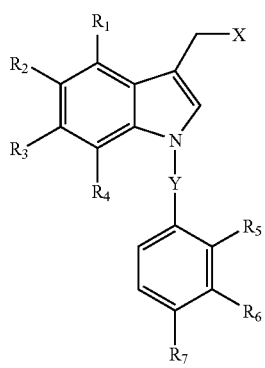

wherein
X is selected from hydroxyl and amino;
Y is carboxyl;
$R_1$, $R_2$, $R_3$, and $R_4$ are selected from hydrogen, halogen, methoxy, trifluoromethyl, hydroxyl and combinations thereof; and
$R_5$, $R_6$, and $R_7$ are selected from hydrogen, chloro, bromo, nitro, phenyl, amino, methoxy, and combinations thereof.

2. The compound of claim 1, wherein $R_1$, $R_2$, $R_3$, and $R_4$ are hydrogen, and X is hydroxyl.

3. The compound of claim 2, wherein the compound is selected from:

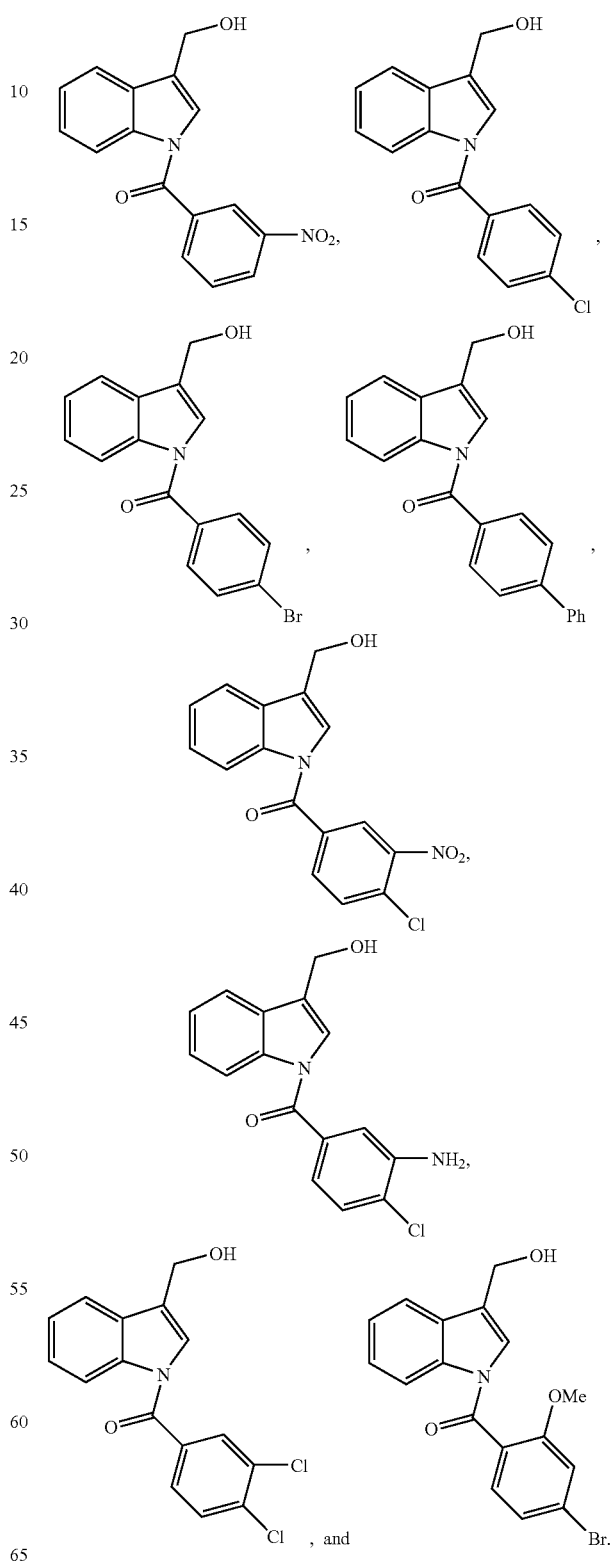

4. A compound selected from:
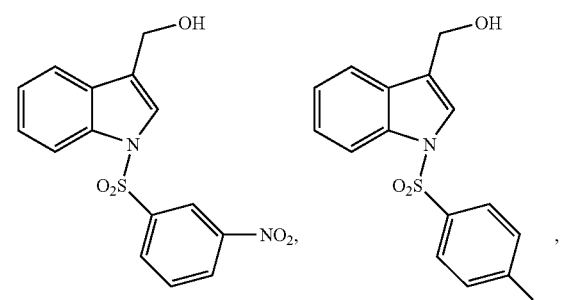
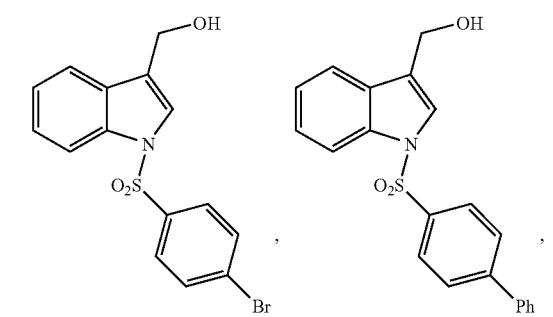
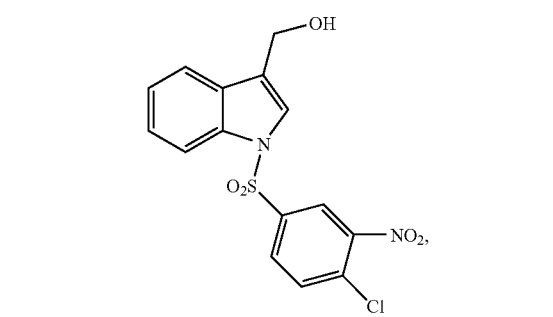
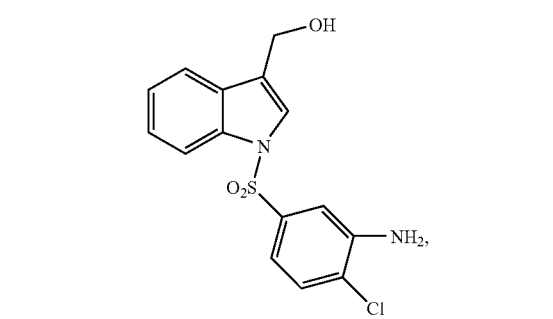
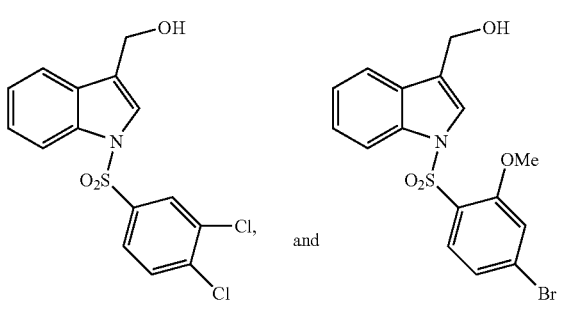
5. The compound of claim 1, wherein $R_1$, $R_2$, $R_3$, and $R_4$ are hydrogen, and X is amino.
6. The compound of claim 5, wherein the compound is selected from:
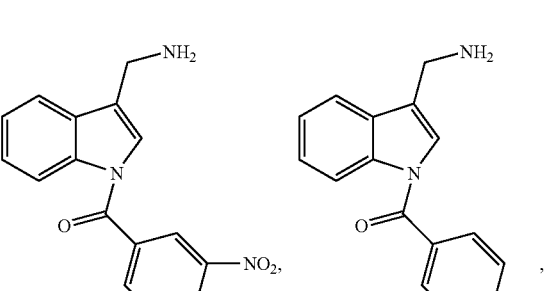
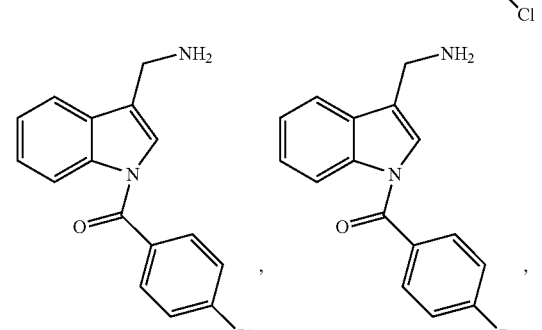
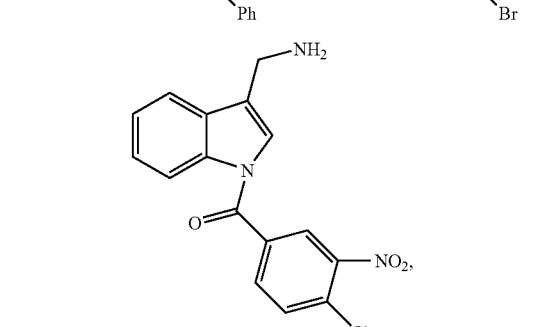
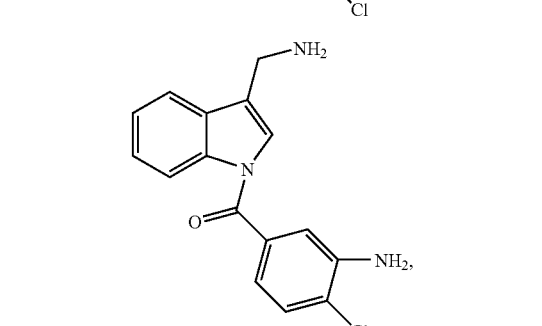
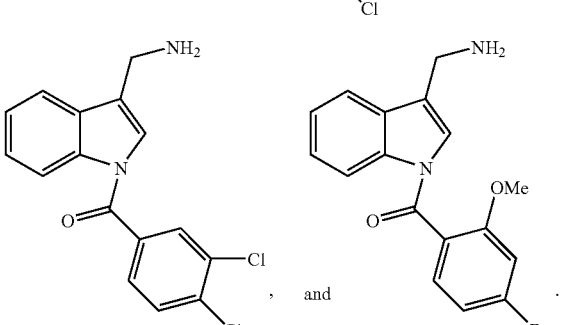

7. A compound selected from:
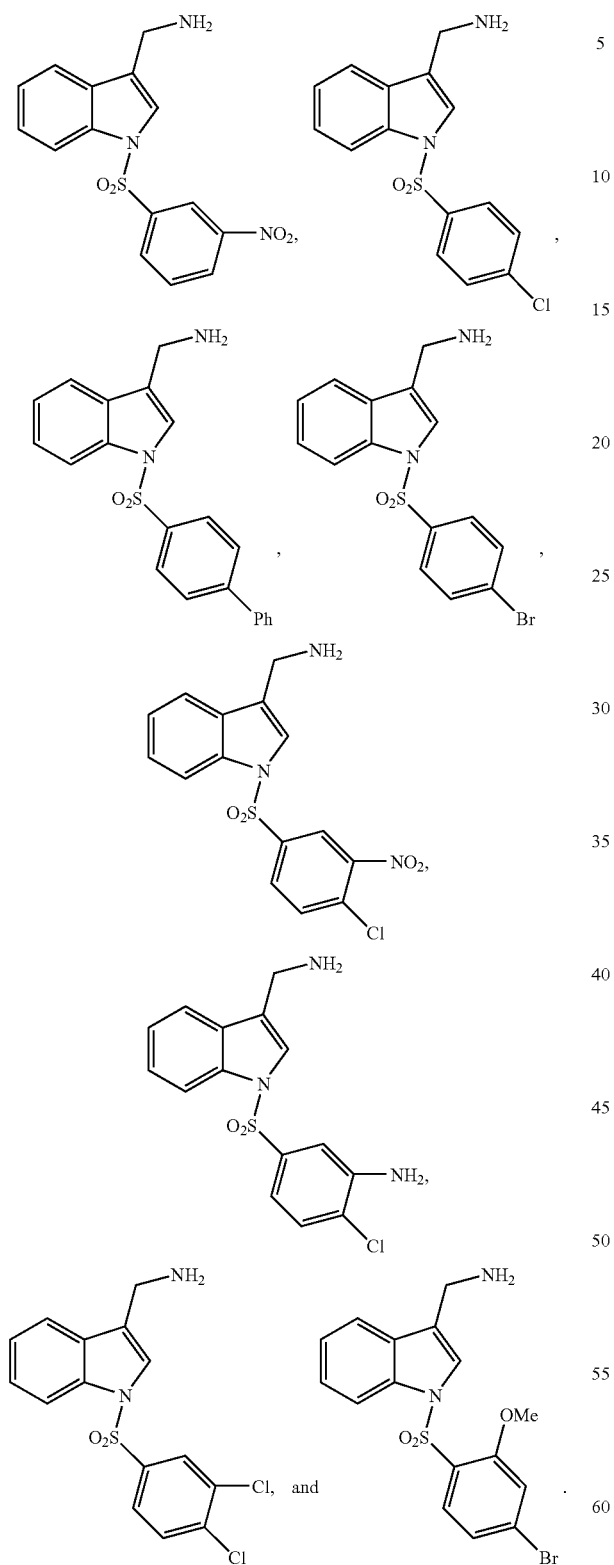
8. The compound of claim 1, wherein $R_5$ is hydrogen, $R_6$ is nitro, $R_7$ is chloro, and X is hydroxyl.
9. The compound of claim 8, wherein the compound is selected from:
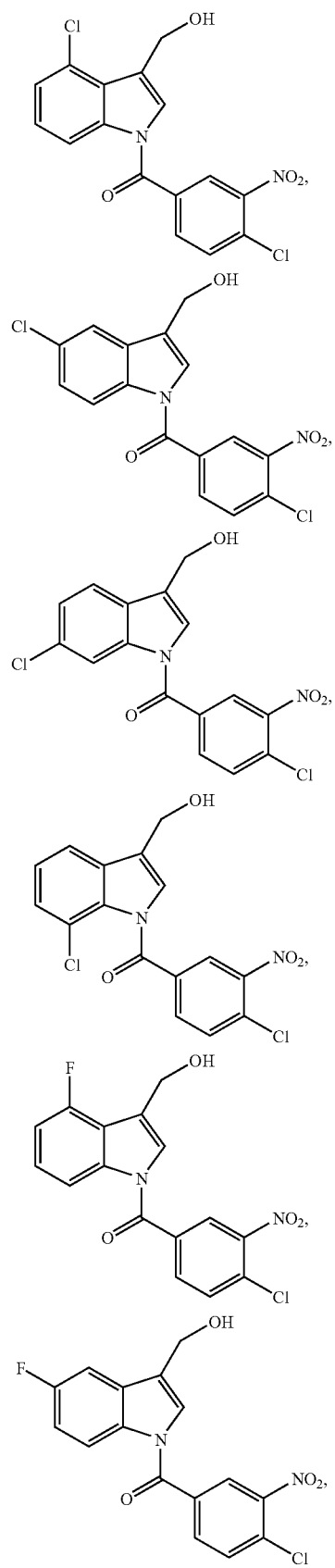

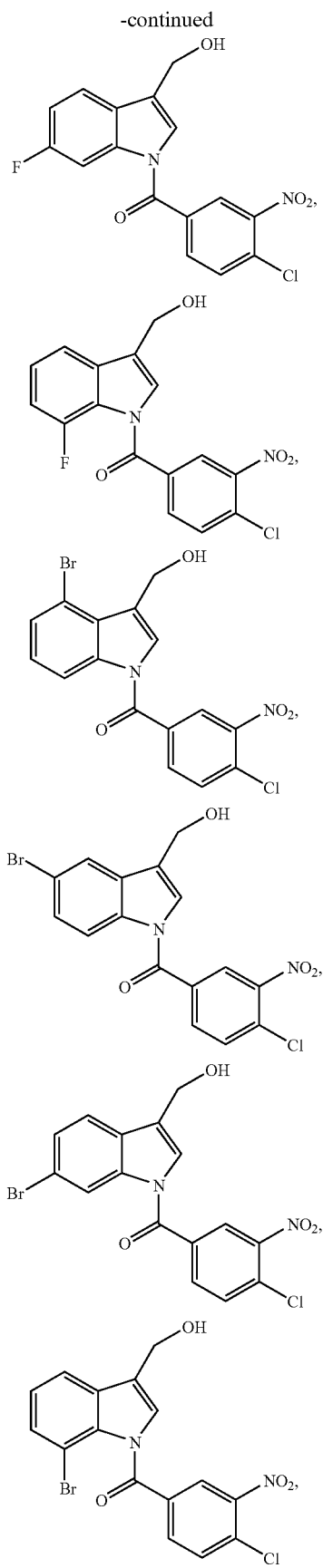
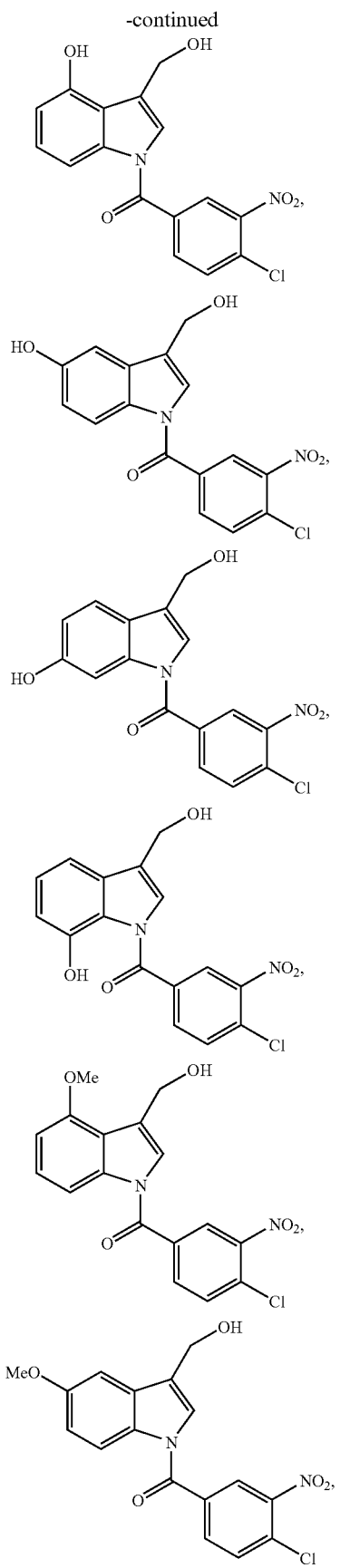

-continued
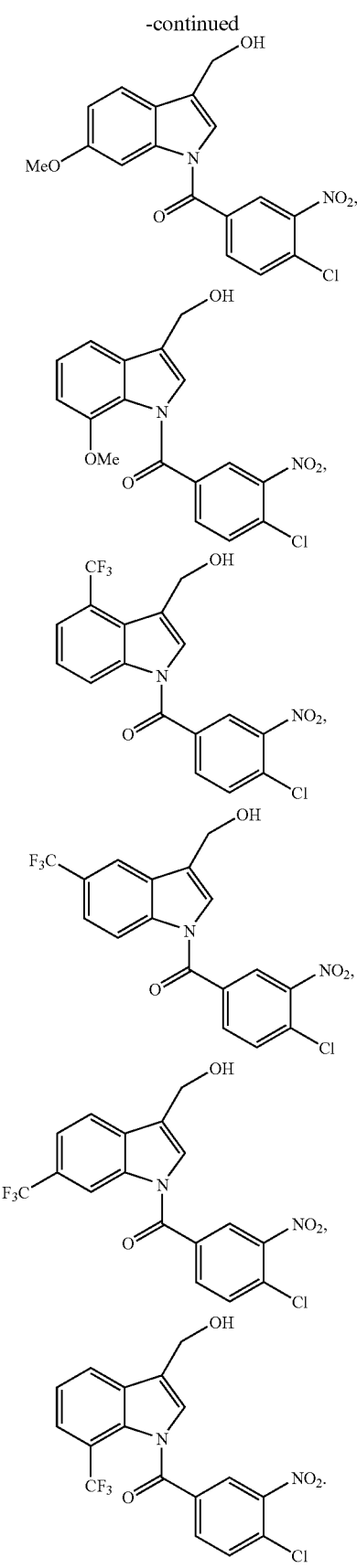
10. A compound of formula I:
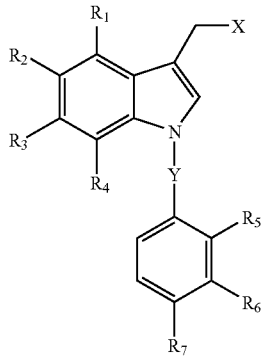
wherein X is hydroxy; Y is sulfonyl;
$R_1$, $R_2$, $R_3$, and $R_4$ are selected from hydrogen, halogen, methoxy, trifluoromethyl, hydroxyl and combinations thereof;
$R_5$ is hydrogen, $R_6$ is nitro, and $R_7$ is chloro.
11. The compound of claim 10, wherein the compound is selected from:
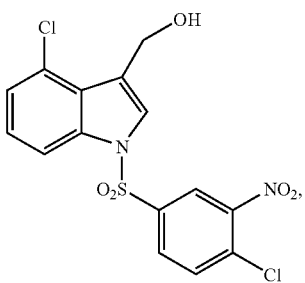
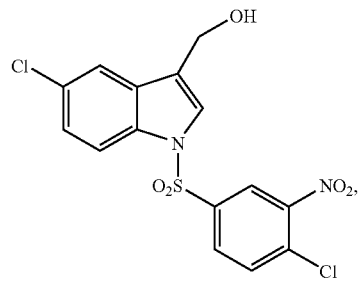
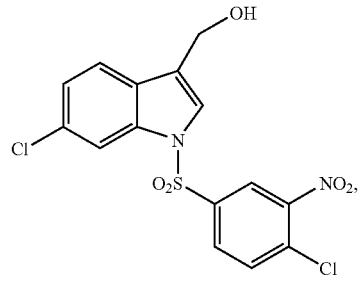

-continued
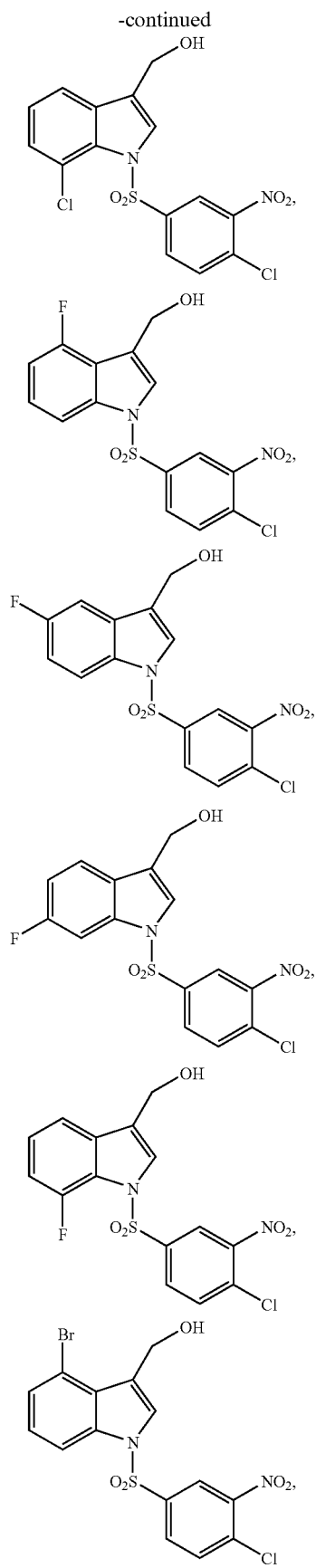
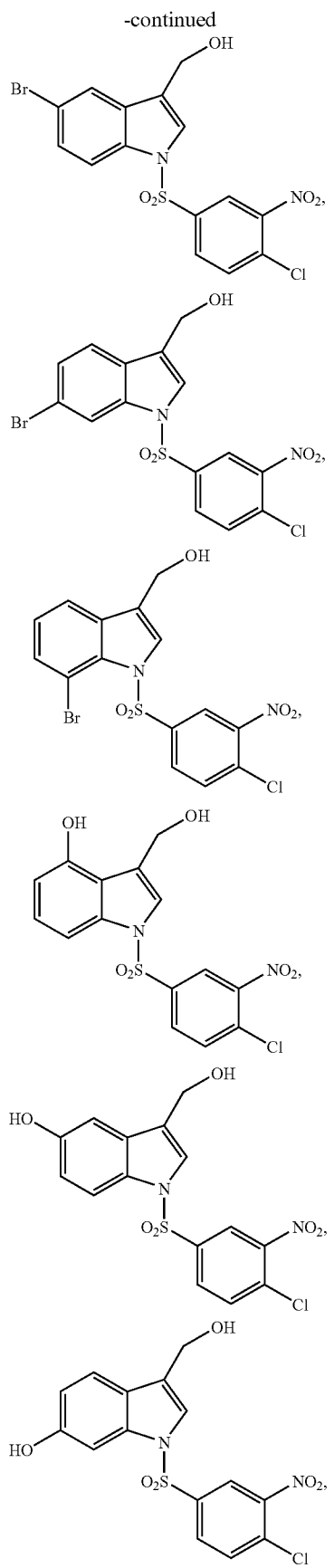

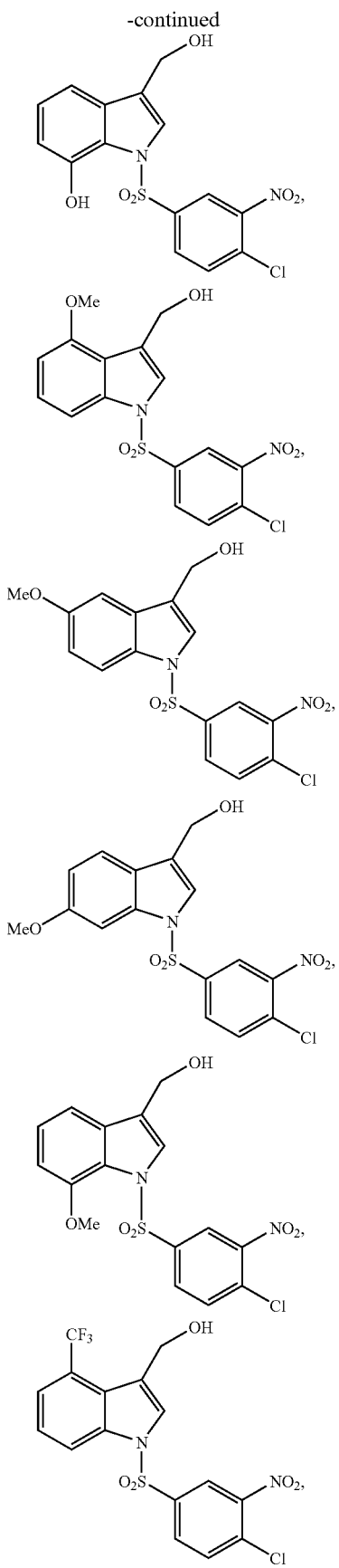
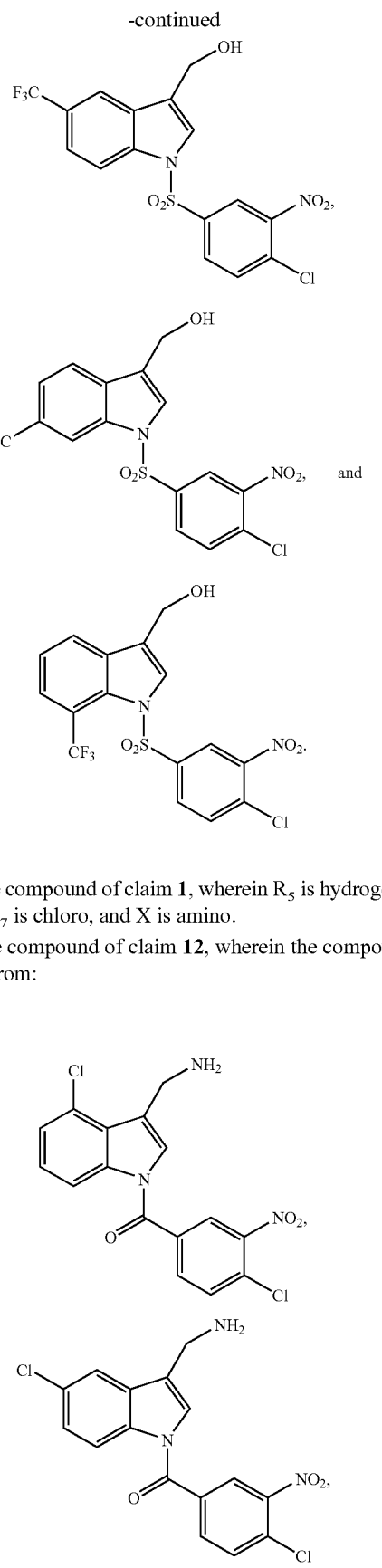
12. The compound of claim 1, wherein $R_5$ is hydrogen, $R_6$ is nitro, $R_7$ is chloro, and X is amino.
13. The compound of claim 12, wherein the compound is selected from:

-continued
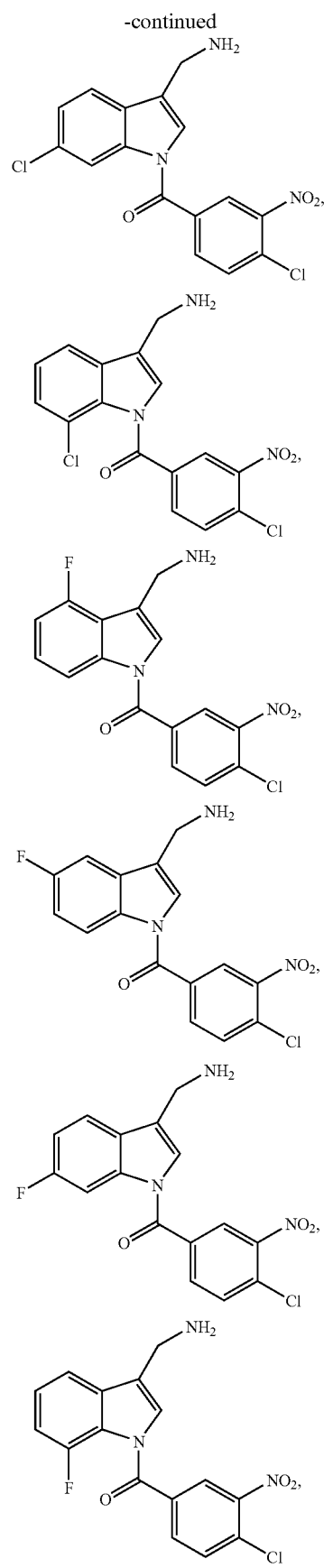
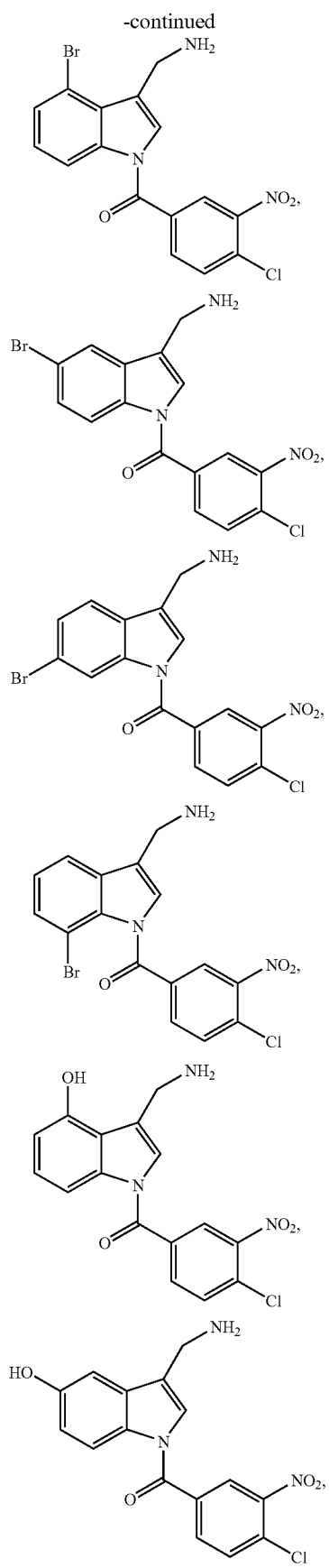

-continued
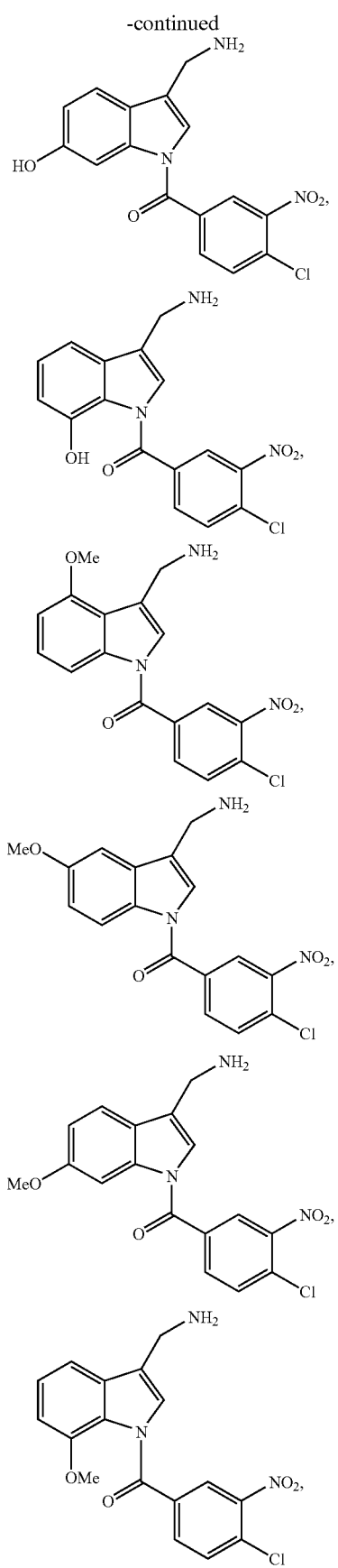
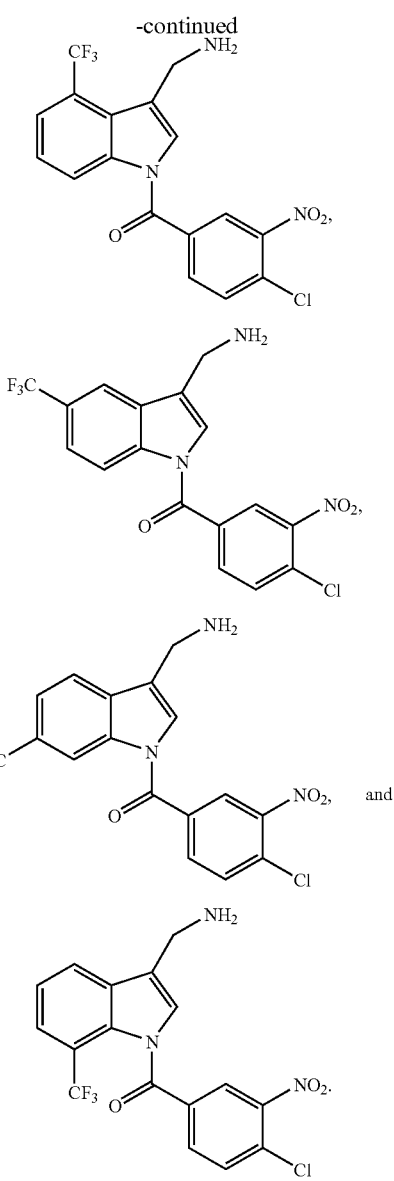
14. A compound of formula I:
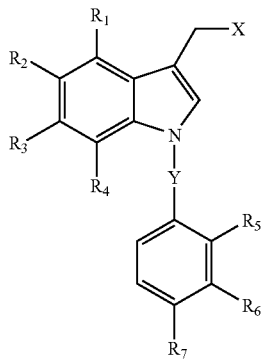

wherein X is amino; Y is sulfonyl;
$R_1$, $R_2$, $R_3$, and $R_4$ are selected from hydrogen, halogen, methoxy, trifluoromethyl, hydroxyl and combinations thereof;
$R_5$ is hydrogen, $R_6$ is nitro, and $R_7$ is chloro.
15. The compound of claim 14, wherein the compound is selected from:
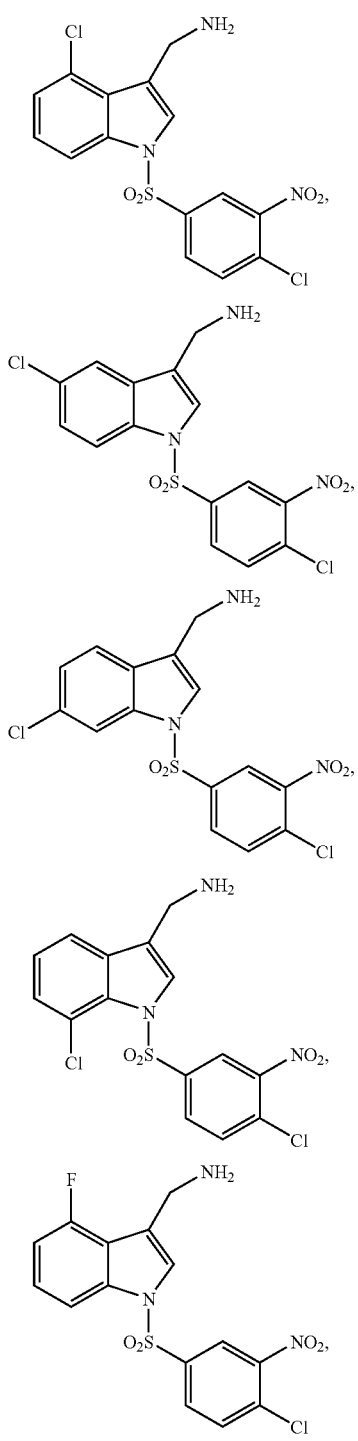
-continued
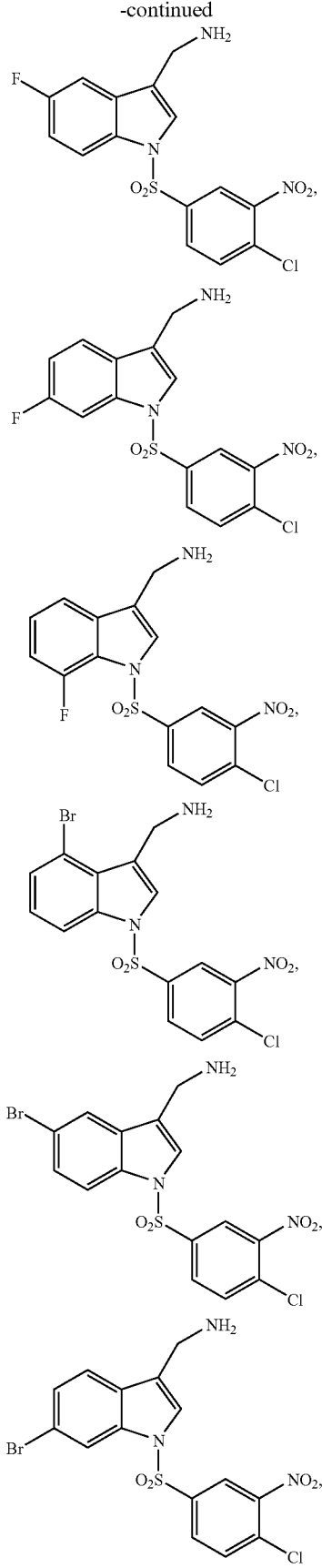

-continued
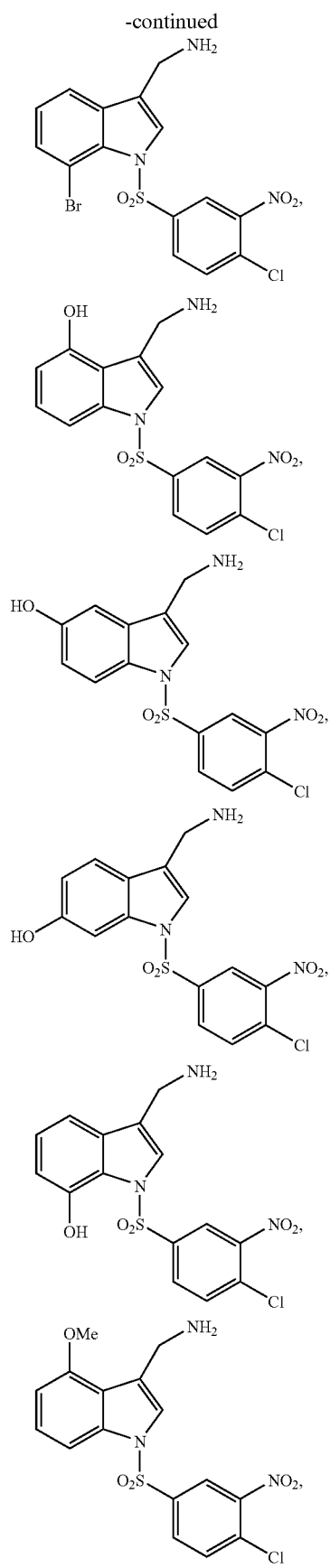
-continued
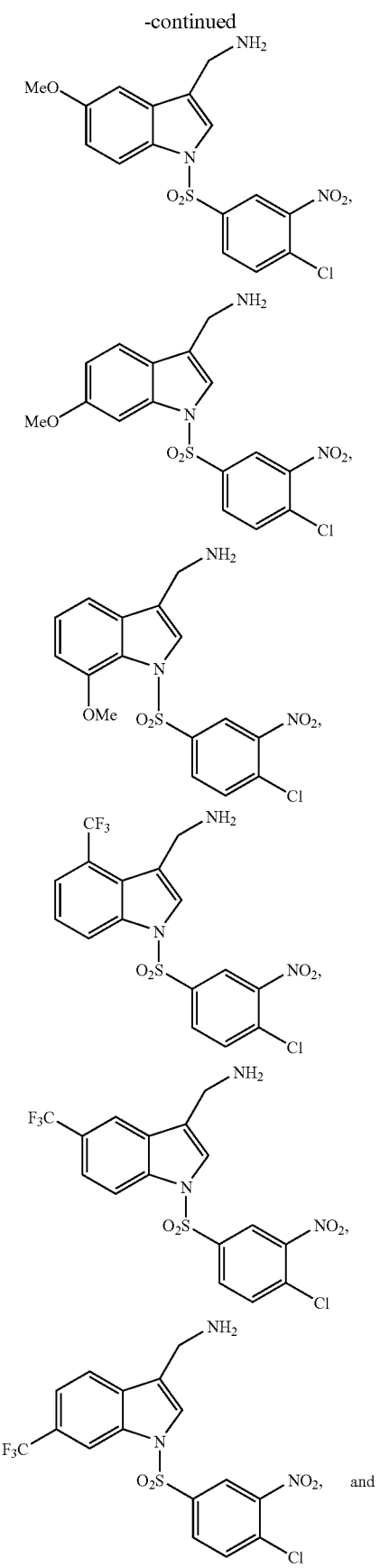

-continued

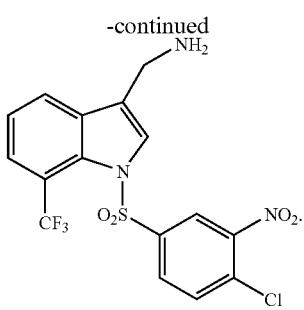

16. A method of inducing apoptosis in rapidly proliferating cells, the method comprising the steps of contacting the rapidly proliferating cells with an effective amount of a compound of formula I:

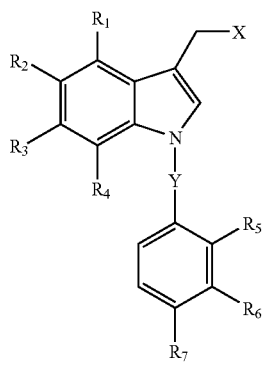

wherein
X is selected from hydroxyl and amino;
Y is selected from carboxyl and sulfonyl;
$R_1$, $R_2$, $R_3$, and $R_4$ are selected from hydrogen, halogen, methoxy, trifluoromethyl, hydroxyl and combinations thereof; and
$R_5$, $R_6$, and $R_7$ are selected from hydrogen, chloro, bromo, nitro, phenyl, amino, methoxy, and combinations thereof.

17. The method of claim 16, wherein the rapidly proliferating cells are in vitro cells.

18. The method of claim 16, wherein the rapidly proliferating cells are prostate cancer cells.

19. A method for treating, inhibiting, or delaying the onset of cancer in a subject in need of such treatment, wherein the method comprises administering a therapeutically effective amount of a compound of formula I:

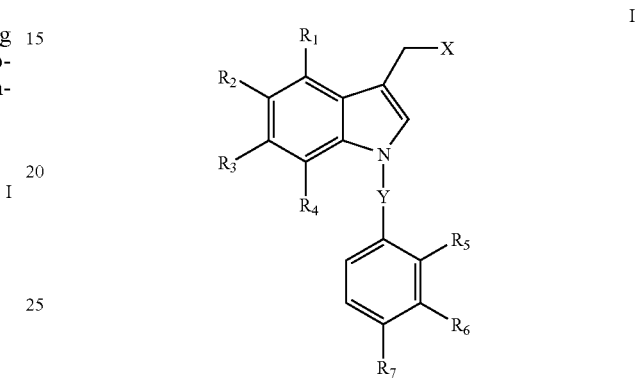

wherein
X is selected from hydroxyl and amino;
Y is selected from carboxyl and sulfonyl;
$R_1$, $R_2$, $R_3$, and $R_4$ are selected from hydrogen, halogen, methoxy, trifluoromethyl, hydroxyl and combinations thereof; and
$R_5$, $R_6$, and $R_7$ are selected from hydrogen, chloro, bromo, nitro, phenyl, amino, methoxy, and combinations thereof; to the subject in need of such treatment, wherein the cancer is prostate cancer.

* * * * *